United States Patent
Kramer et al.

(10) Patent No.: US 11,844,573 B2
(45) Date of Patent: Dec. 19, 2023

(54) ACTIVE VISUAL ALIGNMENT STIMULI IN FUNDUS PHOTOGRAPHY

(71) Applicant: Verily Life Sciences LLC, Mountain View, CA (US)

(72) Inventors: Ryan Kramer, San Francisco, CA (US); Sam Kavusi, Menlo Park, CA (US); Eliezer Glik, San Francisco, CA (US); Seung Ah Lee, San Francisco, CA (US); Chinmay Belthangady, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 132 days.

(21) Appl. No.: 17/321,672

(22) Filed: May 17, 2021

(65) Prior Publication Data

US 2021/0338079 A1    Nov. 4, 2021

Related U.S. Application Data

(63) Continuation of application No. 16/175,719, filed on Oct. 30, 2018, now Pat. No. 11,006,827.

(Continued)

(51) Int. Cl.
| | | |
|---|---|---|
| *A61B 3/15* | (2006.01) | |
| *A61B 3/00* | (2006.01) | |
| *A61B 3/11* | (2006.01) | |
| *A61B 3/113* | (2006.01) | |
| *A61B 3/14* | (2006.01) | |

(Continued)

(52) U.S. Cl.
CPC ............ *A61B 3/152* (2013.01); *A61B 3/0041* (2013.01); *A61B 3/0091* (2013.01); *A61B 3/032* (2013.01); *A61B 3/112* (2013.01); *A61B 3/113* (2013.01); *A61B 3/1225* (2013.01); *A61B 3/145* (2013.01); *A61B 3/0008* (2013.01)

(58) Field of Classification Search
CPC ..... A61B 3/152; A61B 3/0041; A61B 3/0091; A61B 3/032; A61B 3/112; A61B 3/113; A61B 3/1225; A61B 3/145; A61B 3/0008
See application file for complete search history.

(56) References Cited

U.S. PATENT DOCUMENTS

| 6,273,565 B1 | 8/2001 | Matsumoto |
| 6,636,696 B2 | 10/2003 | Saito |

(Continued)

FOREIGN PATENT DOCUMENTS

| CA | 2880856 A1 | 8/2016 |
| CN | 101018501 A | 8/2007 |

(Continued)

OTHER PUBLICATIONS

Chinese Patent Application No. 201880071124.5, Office Action, 11 pages, dated Jan. 26, 2022.

(Continued)

*Primary Examiner* — James C. Jones

(57) ABSTRACT

The technology described herein is directed to a fundus camera and, more specifically, to a fundus camera having a display that projects active visual alignment stimuli onto an eye of an examinee via one or more components of an optimal assembly. The active visual alignment stimuli are dynamically adjusted to guide an examinee toward optical alignment for fundus imaging.

20 Claims, 18 Drawing Sheets

Related U.S. Application Data

(60) Provisional application No. 62/578,771, filed on Oct. 30, 2017.

(51) Int. Cl.
*A61B 3/12* (2006.01)
*A61B 3/032* (2006.01)

(56) References Cited

U.S. PATENT DOCUMENTS

| | | |
|---|---|---|
| 6,755,526 B2 | 6/2004 | Shibata |
| 6,968,127 B2 | 11/2005 | Nanjyo |
| 8,836,778 B2 | 9/2014 | Ignatovich et al. |
| 9,186,293 B2 | 11/2015 | Krenik |
| 2006/0200013 A1 | 9/2006 | Smith et al. |
| 2006/0244972 A1 | 11/2006 | Fercher |
| 2007/0126985 A1 | 6/2007 | Wiltberger et al. |
| 2008/0049188 A1 | 2/2008 | Wiltberger et al. |
| 2008/0212029 A1* | 9/2008 | Ichikawa ............ A61B 3/12 351/208 |
| 2009/0009698 A1 | 1/2009 | Moon et al. |
| 2013/0286346 A1 | 10/2013 | Tsai et al. |
| 2015/0042951 A1 | 2/2015 | Stanga et al. |
| 2015/0223688 A1 | 8/2015 | Wang et al. |
| 2016/0045388 A1 | 2/2016 | Krenik |
| 2016/0296112 A1 | 10/2016 | Fletcher et al. |

FOREIGN PATENT DOCUMENTS

| | | |
|---|---|---|
| CN | 101422355 A | 5/2009 |
| CN | 102283633 A | 12/2011 |
| CN | 102641113 A | 8/2012 |
| CN | 103385691 A | 11/2013 |
| CN | 106164743 A | 11/2016 |
| EP | 1183992 B1 | 12/2005 |
| JP | 2000-139842 A | 5/2000 |
| JP | 2009-172158 A | 8/2009 |
| WO | 2012/082696 A1 | 6/2012 |
| WO | 2015/192079 A1 | 12/2015 |
| WO | 2017/025583 A1 | 2/2017 |

OTHER PUBLICATIONS

International Application No. PCT/US2018/058285, International Search Report & Written Opinion, 11 pages, dated Mar. 7, 2019.
Chinese Patent Application No. 201880071124.5, Notice of Allowance, 5 pages, dated May 16, 2022.
Chinese Patent Application No. 201880071124.5, Office Action, 7 pages, dated Mar. 30, 2022.

* cited by examiner

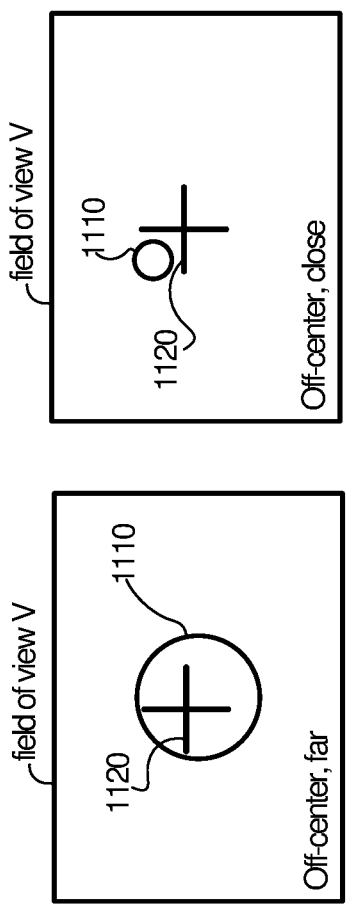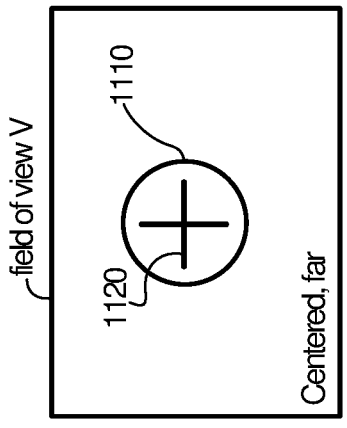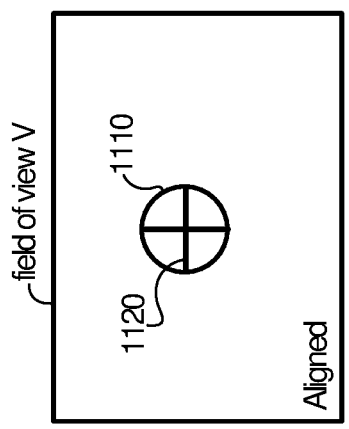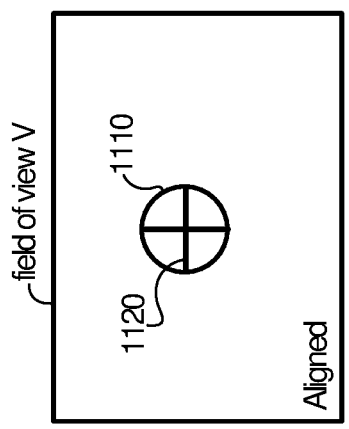

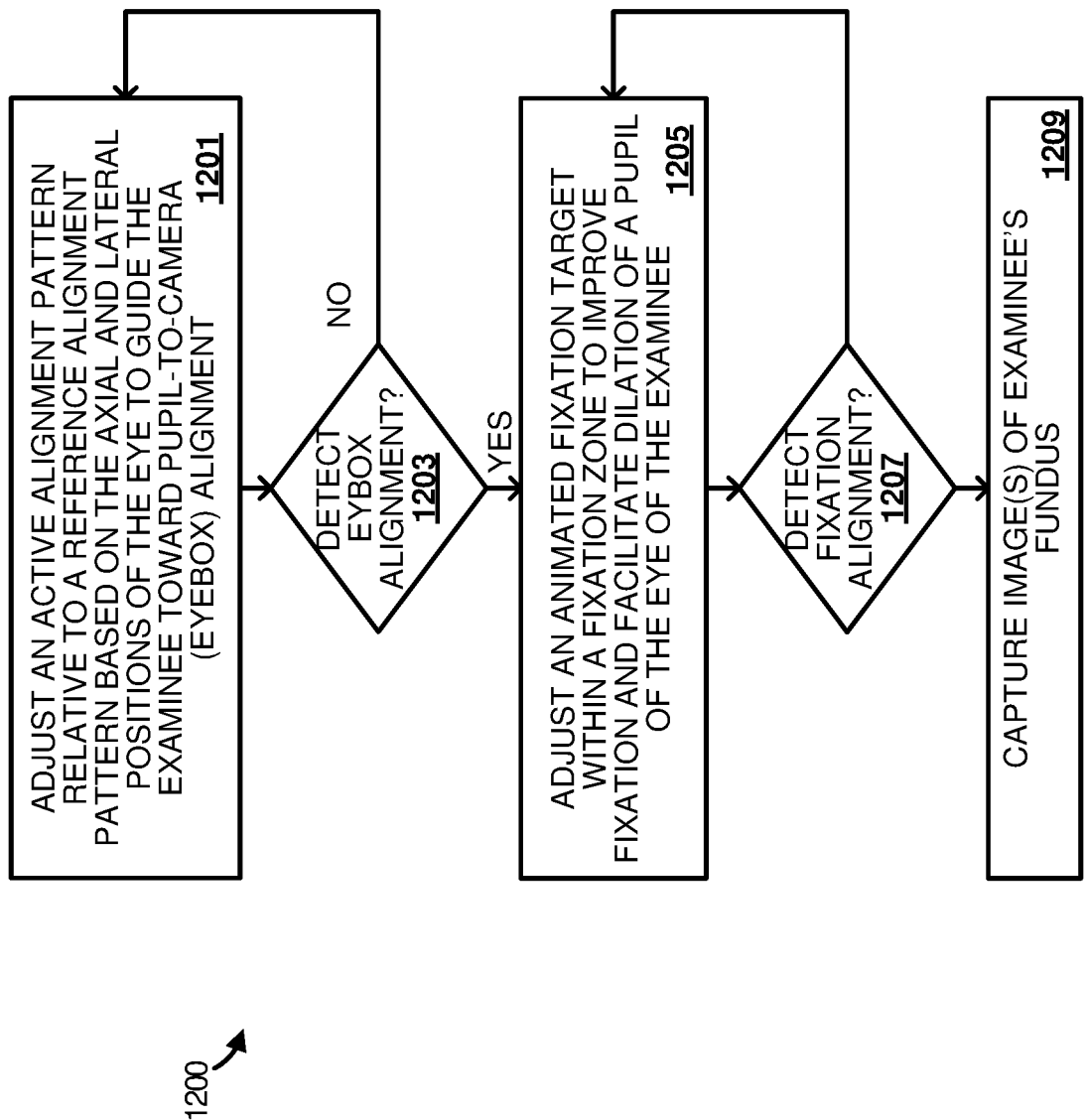

ACTIVE VISUAL ALIGNMENT STIMULI IN FUNDUS PHOTOGRAPHY

CROSS REFERENCE TO RELATED APPLICATIONS

This application is a continuation of U.S. patent application Ser. No. 16/175,719, filed on Oct. 30, 2018, titled "Active Visual Alignment Stimuli In Fundus Photography"; which claims priority to and benefit from U.S. Provisional Patent Application No. 62/578,771, filed on Oct. 30, 2017, titled "Active Visual Alignment Stimuli In Fundus Photography," both of which are expressly incorporated by reference herein.

BACKGROUND

Fundus photography involves capturing a photograph of the back of the eye i.e., the fundus, through the pupil using a specialized fundus camera. A conventional fundus camera typically includes an optical assembly attached to a flash-enabled camera. The optical assembly consists of large, relatively expensive, mechanically movable optics.

High fidelity non-mydriatic fundus imaging requires optical alignment of the eye of the examinee with the optical assembly and the fundus camera. Optical alignment includes pupil-to-camera (or eyebox) alignment and angular (or fixation) alignment. Pupil-to-camera alignment aligns the eye of the examinee axially and laterally in two dimensions with the fundus camera. Likewise, angular alignment aligns the eye of the examinee and the optical assembly by adjusting tilt and pitch for imaging particular structures or regions of the fundus.

In wide-field fundus imaging, the pupil-to-camera alignment margin is so small that achieving alignment typically requires a trained operator or motorized stages. Likewise, angular alignment is difficult to achieve, in part, because the size of the pupil is very small and constantly changing. For example, a young examinee with a purposely dark adjusted eye may have a relatively large pupil through which to image, while the pupil of an older examinee may not dilate as much. Furthermore, in brighter ambient light conditions, the examinee's pupil will shrink making it even more difficult to capture a quality fundus image. Conventional angular alignment includes shining a fixation point onto an examinee's eye and having the examinee stare at the fixation point as intently as possible. Unfortunately, it is often difficult and uncomfortable for an examinee to focus on a single point of light for an extended period. This level of intense focus can, and often does, result in micro-saccadic movements, e.g., inadvertent back and forth eye movements, that cause inconsistent fixation. These movements, as well as other issues with the conventional alignment process, can result in unusable fundus images, e.g., images that do not capture a necessary field of view, include motion artifacts, etc.

BRIEF DESCRIPTION OF THE DRAWINGS

A detailed description is set forth and will be rendered by reference to specific examples thereof which are illustrated in the appended drawings. Understanding that these drawings depict only typical examples and are not therefore to be considered to be limiting of its scope, implementations will be described and explained with additional specificity and detail through the use of the accompanying drawings.

FIGS. 11A-11D depict example active visual alignment stimuli that are projected onto an eye of an examinee within a field of view for guiding or steering the examinee's line of sight toward pupil-to-camera alignment, according to some implementations.

FIG. 12 depicts a flow diagram illustrating example operations of a fundus camera having a display operable to project active visual alignment stimuli, according to some implementations.

Figure 1A:
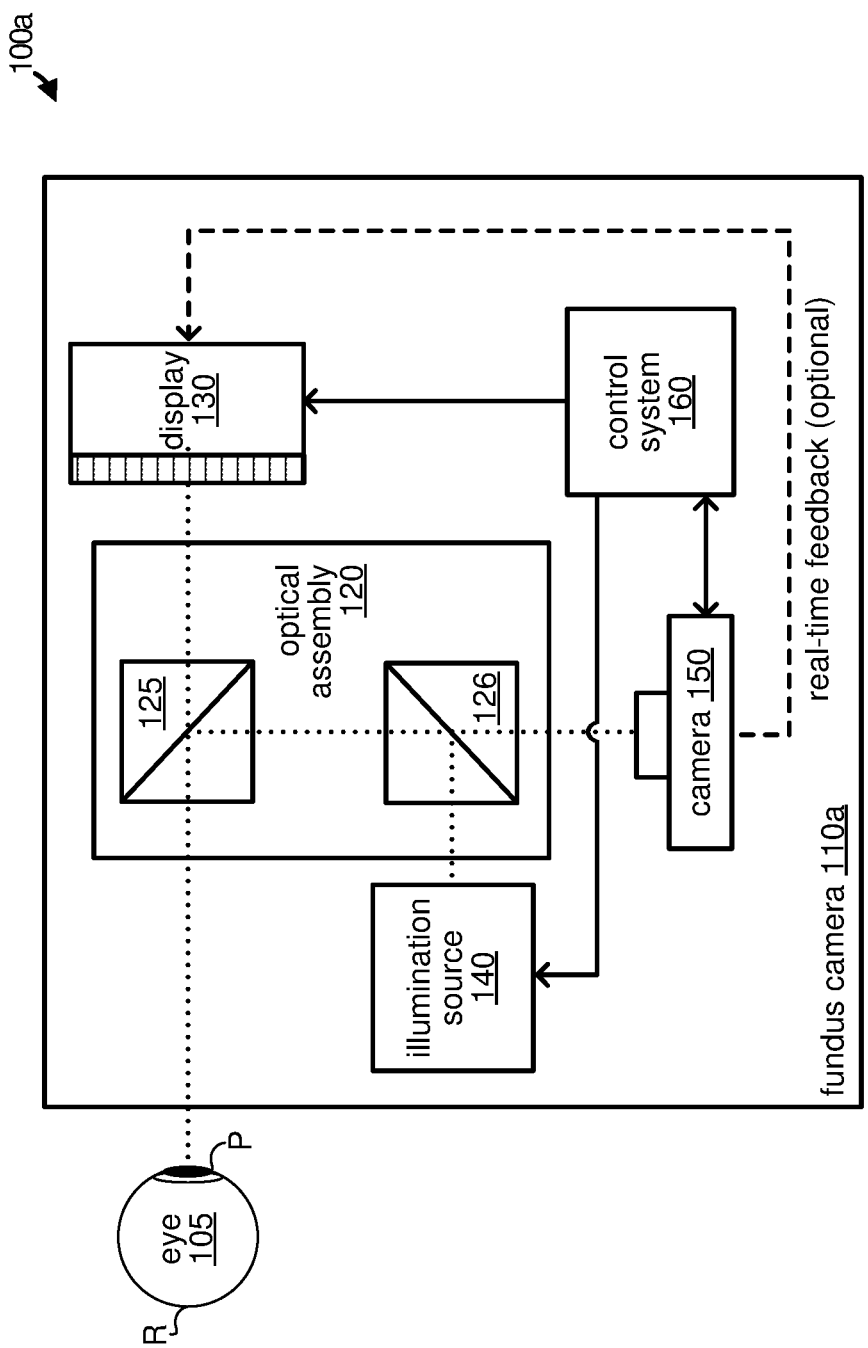
FIGS. 1A and 1B depict block diagrams illustrating example schematic architectures for fundus cameras including a display for presenting an animated fixation target onto an eye of an examinee for fundus imaging, according to some implementations.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Examples are discussed in detail below. While specific implementations are discussed, it should be understood that this is done for illustration purposes only. A person skilled in the relevant art will recognize that other components and configurations may be used without parting from the spirit and scope of the subject matter of this disclosure. The implementations may include machine-implemented methods, computing devices, or computer readable medium.

Examples discussed herein relate to a fundus camera and, more specifically, to a fundus camera having one or more embedded or included displays that project active visual alignment stimuli onto an eye of an examinee e.g., a patient, via one or more components of an optimal assembly to guide the examinee toward optical alignment for capturing fundus images.

In some implementations, the fundus camera includes a display that projects an animated fixation target (or other image) onto an eye of an examinee via one or more components of an optimal assembly. The animated fixation target is dynamically adjusted within a fixation zone (or perimeter) to provide comfort to the examinee while gradually guiding or steering the examinee's eye toward optical alignment of the eye of the examinee with the optical assembly and the fundus camera for fundus imaging.

In some implementations, the fundus camera includes a tracking camera (or component) that can track the location and/or size of the examinee's pupil while the fixation target is being dynamically adjusted. The output of the tracking camera is fed to an opportunistic alignment mechanism for determination of an optimal time for triggering the fundus imaging process, e.g., for maximizing pupil size during the imaging process. For example, the tracking camera can continuously monitor the retina of the examinee to determine when alignment is reached while the animated fixation target guides or steers the examinee toward alignment. Among other benefits, the fundus camera increases accuracy and fixation while decreasing the amount of time required for fundus image capture. Additionally, the fundus camera removes the need for a separate fundus camera operator.

In some implementations, the fundus camera can monitor the time of adaptation and automatically increases the illumination if the response time is greater than a threshold. In this manner, the fundus camera detects a "sweet spot," e.g., before the iris has adapted to the dark conditions but before the rod response commences. This functionality avoids triggering a chemical rod response and thereby minimizes discomfort to the examinee.

In some implementations, the tracking camera can track the pupil becoming larger over time and when the pupil has stopped growing, but before the dark-adaptation commences, a control system can trigger the imaging process, e.g., trigger a flash and capture one or more fundus images during the flash. In some implementations, the tracking camera can track pupil size and trigger the imaging process once a threshold pupil size is exceeded, e.g., 5 millimeters may be sufficient for fundus imaging irrespective of the individual rate of change or maximum pupil size.

In some implementations, real-time (or near real-time) feedback is provided via a display for visualization of one's own fundus by an examinee. The real-time feedback enables a "selfie-mode" whereby the examinee can manually trigger the fundus imaging process. Additionally, one or more camera state indicators can be shown to the examinee so that the examinee maintains focus and is not surprised, e.g., by the camera flash.

Among other benefits, the fundus camera discussed herein increases dilation of an examinee's pupil without medication and optimizes the examinee's fixation and stability during fundus imaging while maintaining the examinee's eye in a comfortable mesopic state using small, low-cost optics. In addition, the fundus camera strategically and, in some instances, automatically, triggers the image capture process at the appropriate time. These improvements, among others, facilitate a relatively low-cost, high fidelity non-mydriatic fundus camera.

Figure 1B:
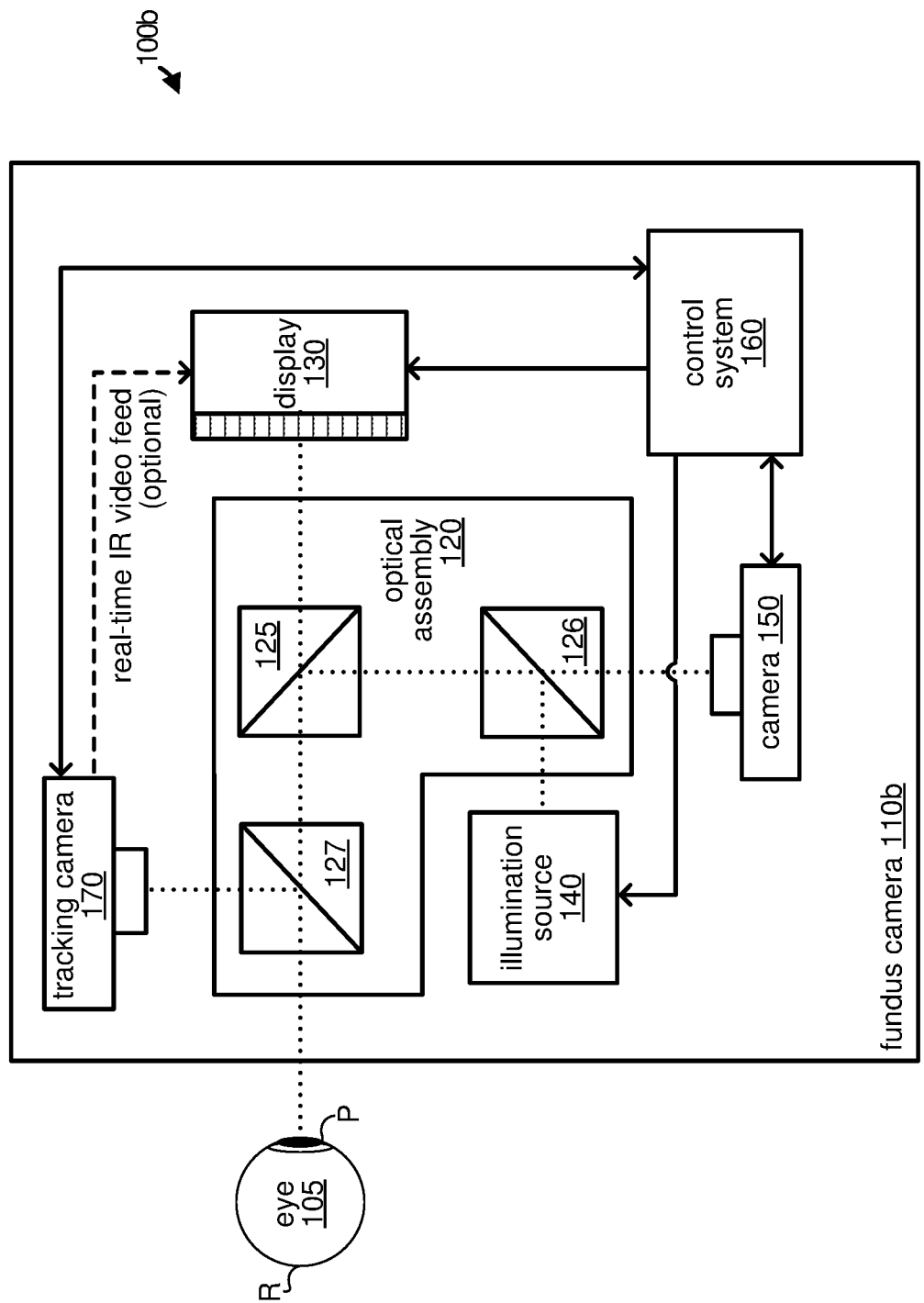

FIG. 1A and FIG. 1B depict block diagrams illustrating example schematic architectures 100a and 100b for fundus cameras 110a and 110b, respectively, including a display 130 for presenting an animated fixation target onto an eye 105 of an examinee for fundus imaging, according to some implementations. Referring first to FIG. 1A, fundus camera 110a includes optical assembly 120, display 130, illumination source 140, camera 150 and control system 160. Additional or fewer components are possible.

The optical assembly 120 includes half mirrors 125 and 126. As noted above, traditional fundus cameras include relatively large, expensive, mechanically movable optics. Conversely, optical assembly 120 includes smaller, less expensive, fixed optics. The optical assembly 120 may be constructed in the form of a cylindrically-shaped optomechanical tube that an examinee can look through for fundus imaging. Although not shown, the optical assembly 120 can include a housing.

The display 130 is operable to project an animated fixation target or other image onto a retina R of an examinee's eye 105 via one or more components of the optimal assembly 120. The fixation target can be displayed or presented within a fixation zone (or perimeter) to guide or steer an examinee's line of sight toward alignment for fundus imaging. Display 130 can be any small, high-resolution electronic display, e.g., OLED, LCD, display with micromirrors on glass or silicon with the ability to provide high contrast and color, etc., designed for use in near-eye applications. In some implementations, display 130 can be a microdisplay.

As shown in the example of FIG. 1A, display 130 is in communication with control system 160. Control system 160 directs display 130 to dynamically adjust the image within a fixation zone (or perimeter) and/or adjust the fixation zone (or perimeter) itself to steer or guide the examinee's line of sight toward fixation alignment. As discussed herein, the phrase "dynamically adjusting the image" or variations thereof means altering or moving the image slightly to achieve the desired appearance on the display. Dynamic adjustments can also include adaptations of the image, e.g., from one image to another, various movements of the image, etc. For example, the image can be dynamically adjusted based on new input that was previously unknown, e.g., new input from an eye tracker.

The fixation target can be one or more objects or images strategically selected to maximize dilation of the examinee's pupil P and optimize the examinee's fixation and stability during fundus imaging while maintaining the examinee's eye in a comfortable mesopic state. In some implementations, the fundus camera achieves increased pupil dilation of the eye of the examinee by rendering a pattern (or fixation target) with a specific modulation transfer function (MTF) or spatial frequency content. The MTF is the spatial frequency response of an imaging system or a component thereof.

Additionally, the fixation target can be strategically selected to cause the examinee to increase intensity of focus (and/or other types of emotional arousal) which thereby maximize the size of pupil P for fundus imaging. For example, the control system 160 can control the intensity of each individual pixel of the display 130 in a manner that facilitates increasing the size of pupil P. The control system 160 can also direct the display 130 to alter ambient lighting conditions to cause the eye 105 to increase intensity of focus and/or cause the pupil P to expand for fundus imaging. For example, the display can project a purely black background as opposed to a dimly lit red background and/or alter or vary the background as necessary.

The illumination source 140 can be any light source that emits illumination light and/or otherwise provides a light (or flash) for capturing fundus images via camera 150. As shown in the example of FIG. 1A, the illumination light is projected onto eye 105 of the examinee by one or more components of optical assembly 120. Camera 150 can be any camera configured to capture images of the fundus via optical assembly 120. In some implementations, camera 150 can be a high-speed camera that enables multiple images or frames to be taken during an extended flash.

The control system 160 is operably coupled with various components of fundus camera 110a for providing control information and/or receiving feedback. As shown in the example of FIG. 1A, the control system 160 is operably coupled with display 130, illumination source 140 and camera 150. In some implementations, the control system 160 monitors fixation alignment and commences fundus imaging once fixation alignment is achieved. For example, once fixation alignment is properly achieved, the control system 160 directs the illumination source 140 to emit a flash and the camera 150 to capture multiple images during the flash.

In some implementations, the illumination source 140 is configured to emit an extended flash, e.g., 100-200 milliseconds or longer, so that camera 150 can capture multiple frames, e.g., 50 or more frames or images. It is appreciated that, although the flash is extended, a typical examinee would not likely notice a difference between the extended flash and an instantaneous flash.

The speed of camera 150 enables a high-speed imaging pipeline that facilities capture of the multiple images during the extended flash. Conversely, traditional fundus cameras emit a very bright, instantaneous flash to capture a single fundus image from a slower camera. As noted above, if camera 150 happens to be misaligned during the image capture window, or if the examinee's eye 105 moves, then the image may end up with motion artifacts or aberrations resulting in blurry or unusable photos.

In some implementations, control system 160 can work in conjunction with camera 150 to enable the high-speed imaging pipeline. The control system 160 performs various post-processing procedures on the images. For example, the control system 160 analyzes the frames obtained from camera 150, stacks them together to correct for any motion artifacts or aberrations, throws out frames that are bad or unusable, auto selects for the best frames, and stacks the remaining images back together into a composite image. The control system 160 can drive the display 130 to maintain the animated fixation target for the duration of the extended flash to keep the examinee fixated and thereby avoid motion artifacts or aberrations during the imaging process.

In some implementations, the control system 160 directs the camera 150 to provide real-time feedback to the display 130 so that the examinee has a real-time (or near real-time) visualization of what images can be captured at any given point in time. The real-time feedback may be provided to display 130 by way of one or more components of control system 160 and/or by way of a direct channel from the camera 150 to the display 130. In some implementations, the real-time feedback allows the examinee to manually trigger the fundus imaging, e.g., selfie-mode.

Control system 160 is representative of any processing, computing system or other circuitry that retrieves and executes software suitable for carrying out a service or collection of services to capture high-fidelity fundus images as discussed herein. Control system 160 can include one or more general purpose central processing units, graphic processing units, application specific processors, and logic devices, as well as any other type of processing device, combinations, or variations thereof.

Referring next to FIG. 1B, FIG. 1B depicts a block diagram illustrating an example schematic architecture of fundus camera 110b including a display 130 for presenting an animated fixation target onto an eye 105 of an examinee for retinal imaging, according to some implementations. Fundus camera 110b includes many of the components of fundus camera 110a of FIG. 1A, but also includes a tracking camera 170.

Tracking camera 170 can be any camera configured to continuously track and/or monitor the pupil P of an examinee via one or more components of optical assembly 120. For example, tracking camera 170 can use infrared (IR) to track the eye 105, e.g., pupil P, retina R, etc. As shown in the example of FIG. 1B, tracking camera 170 tracks or monitors pupil P via half mirror 127. The tracking information can be sent to control system 160 to determine the precise time when fixation alignment is reached.

While the fundus camera 110b is attempting to achieve fixation alignment, e.g., the examinee is staring down the optical tube, the tracking camera 170 visualizes the eye 105 in real-time and the control system 160 determines if the examinee is properly fixated. In some implementations, the tracking camera 170 provides a continuous video stream of the examinee's fixation. The control system 160 processes the feedback information, e.g., video stream, and directs the display 130 to project a fixation target to show the examinee where to look and how to fixate.

As noted above, the display 130 allows the fundus camera to project a complete image onto the retina R of examinee's eye 105. Similarly, the high-speed imaging pipeline facilitates real-time feedback to be fed to the display 130. Accordingly, in some implementations, control system 160 is configured to direct the display 130 to project an infrared view of the eye 105 back to the examinee in real time. That is, the examinee can view his or her own retina—essentially like looking in the mirror—but in infrared. This allows for very precise alignment as the examinee can entirely self-align, e.g., without an operator.

In some implementations, the display 130 provides camera state indicators to the examinee so that an examinee knows when he or she is properly aligned or when the camera flash is going off so that the examinee is not startled. The camera state indicators can be small graphics, colors, etc., that are predetermined to indicate a state of the fundus camera or progress of alignment therewith.

In some implementations, the fixation target can be strategically animated based on the opportunistic alignment mechanism. That is, when the opportunistic alignment mechanism determines that the examinee is close to alignment, the fixation target animation can be steered or guided toward a final state, e.g., a single fixation point within fixation zone that matches the final alignment. Alternatively, in some implementations, the final state can include the fixation zone itself shrinking to a single fixation point. As discussed herein, the phrase "based on" means based at least partially or wholly on.

Figure 2:
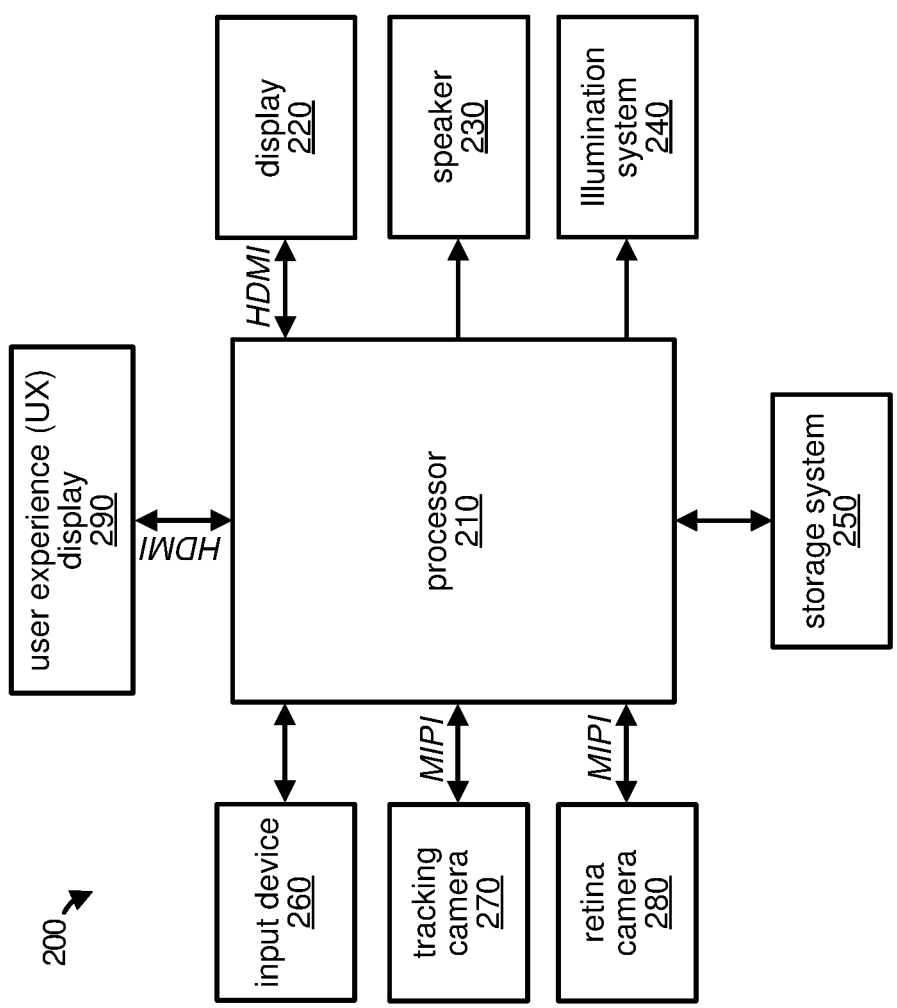
FIG. 2 depicts a block diagram illustrating example components of a fundus camera, according to some implementations.

FIG. 2 depicts a block diagram illustrating example components of a fundus camera 200, according to some implementations. Fundus camera 200 can be fundus camera 110a of FIG. 1A or 110b of FIG. 1B, although alternative configurations are possible. As shown in the example of FIG. 2, the fundus camera 200 includes processor 210, display 220, speaker 230, illumination system 240, storage system 250, input device 260, tracking camera 270, retina camera 280, and user experience (UX) display 290. Additional or fewer components are possible.

The processor 210 is representative of any processing, computing system or other circuitry that retrieves and executes software from storage system 250 suitable for carrying out a service or collection of services that produce high-fidelity fundus images as discussed herein. For example, processor 201 accesses, monitors, or otherwise receives input from other components of the fundus camera to control the components and provide Examples of processor 210 include general purpose central processing units, graphic processing units, application specific processors, and logic devices, as well as any other type of processing device, combinations, or variations thereof.

The display 220 is representative of any small, high-resolution electronic display designed for use in near-eye applications. As discussed herein, the display includes various components for rendering animated fixation targets to an examinee and dynamically adjusting the animated fixation targets.

The speaker 230 is representative of any audible device capable of making sound for notifying an examinee about internal states of the fundus camera, e.g., alignment, flash, etc.

The illumination system 240 is representative of any light source that emits illumination light and/or otherwise provides a flash for capturing fundus images via retina camera 280.

The memory 250 is representative of any memory system that stores instructions for operation and storage memory for captured fundus images. The memory 250 can be any device, mechanism, or populated data structure used for storing information. In some implementations, memory 250 can encompass any type of, but is not limited to, volatile memory, nonvolatile memory and dynamic memory. For example, memory 250 can be random access memory, memory storage devices, optical memory devices, media magnetic media, floppy disks, magnetic tapes, hard drives, SDRAM, RDRAM, DDR RAM, erasable programmable read-only memories (EPROMs), electrically erasable programmable read-only memories (EEPROMs), compact disks, DVDs, and/or the like. Memory 250 may include one or more disk drives, flash drives, one or more databases, one or more tables, one or more files, local cache memories, processor cache memories, relational databases, flat databases, and/or the like. In addition, those of ordinary skill in the art will appreciate many additional devices and techniques for storing information which can be used as memory 250.

The input device 260 is representative of any device or other circuitry that receives external input from an operator of the fundus camera and/or an examinee. For example, the input device 260 can include a microphone, clicker for triggering imaging, keyboard or other input device.

The tracking camera 270 is representative of any camera, IR or near-IR tracking device, e.g., any wavelength above 820 nanometers, or image sensor capable of tracking the examinee's eye. For example, tracking camera 270 can use infrared (IR) to track and/or monitor one or more parts of the examinee's eye. As discussed herein, the tracking information and/or video stream can be used by processor 210 to determine the precise time when fixation alignment is reached. Additionally, the IR video stream can be fed to display 220 for real-time projection back to the examinee.

The user experience (UX) display 290 is representative of any external monitor or touchscreen that interacts with the fundus camera. In some implementations, an operator of fundus camera 200 can use the UX display 290 to visualize alignment, trigger fundus imaging, control the animated fixation target(s) or other images (including video feedback) that are projected by the display 220, etc.

Figure 3:
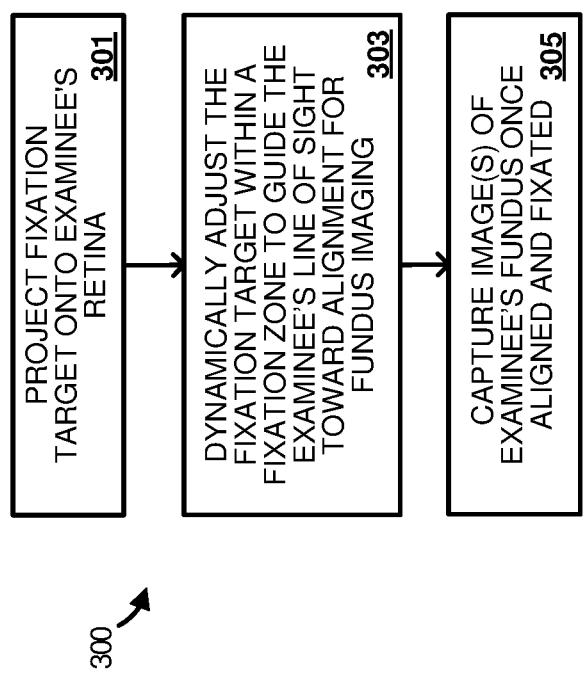
FIG. 3 depicts a flow diagram illustrating example operations of a fundus camera having a display, according to some implementations.

FIG. 3 depicts a flow diagram illustrating example operations 300 of a fundus camera having a display, according to some implementations. More specifically, the example of FIG. 3 depicts operations of a fundus camera having a display for projecting an animated fixation target onto an eye of an examinee for guiding or steering an examinee's line of sight toward alignment for fundus imaging. The example operations 300 may be performed in various implementations by a fundus camera such as, for example, fundus camera 110a or 110b of FIG. 1A or FIG. 1B, respectively, or one or more processors, modules, engines, or components associated therewith.

To begin, at 301, the fundus camera directs the display to project a fixation target onto an examinee's retina. At 303, the fundus camera dynamically adjusts the fixation target within the fixation zone to guide the examinee's line of sight toward alignment for fundus imaging. Lastly, at 305, once aligned and fixated, the fundus camera captures images of the examinee's fundus.

Figure 4:
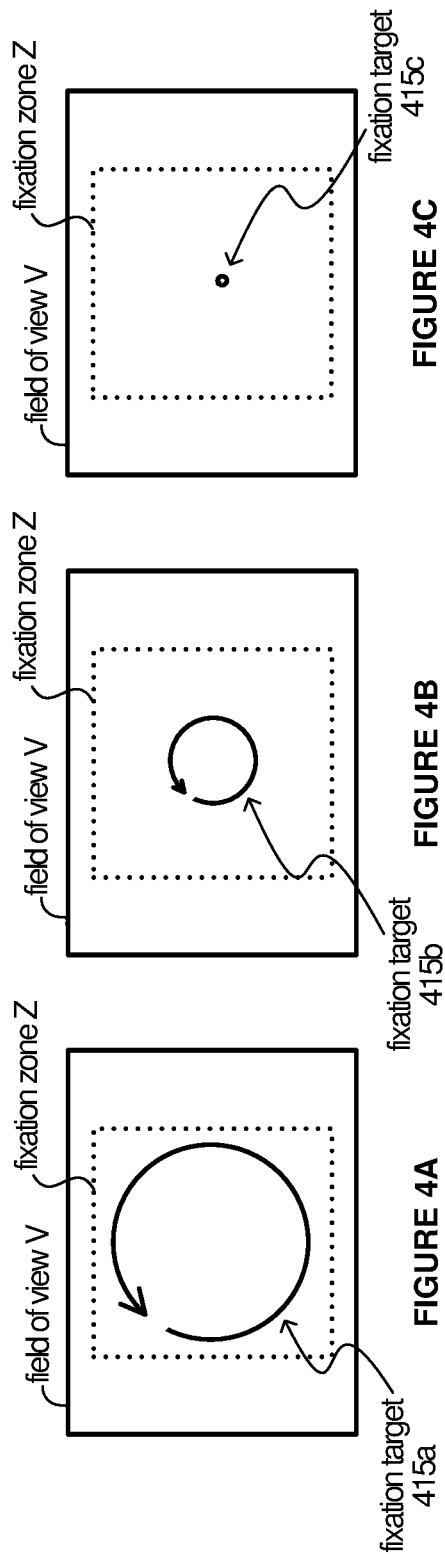
FIGS. 4A, 4B, and 4C depict progression of an example animated fixation target within a fixation zone of a viewing area for guiding or steering an examinee's line of sight toward alignment for fundus imaging, according to some implementations.

FIGS. 4A-4C depict progression of an example animated fixation target 415 within a fixation zone Z of a viewing area V for guiding or steering an examinee's line of sight toward fixation alignment for fundus imaging, according to some implementations.

Viewing area V comprises a range of view of an examinee's eye while looking into an opening of a fundus camera for retinal imaging. As shown in the example of FIGS. 4A-4C, the animated fixation target is a rotating circle that gets smaller and smaller until it hits a fixation point. The rotating circle gently guides or steers the examinee's eye toward the fixation point. In some implementations, the control system monitors the progress of fixation alignment and thereby dynamically controls the speed of rotation of the circle, the speed of shrinking of the circle, the ambient background, etc., of the image projected to the eye such that fixation alignment is achieved as quickly and painlessly as possible.

Figure 5:
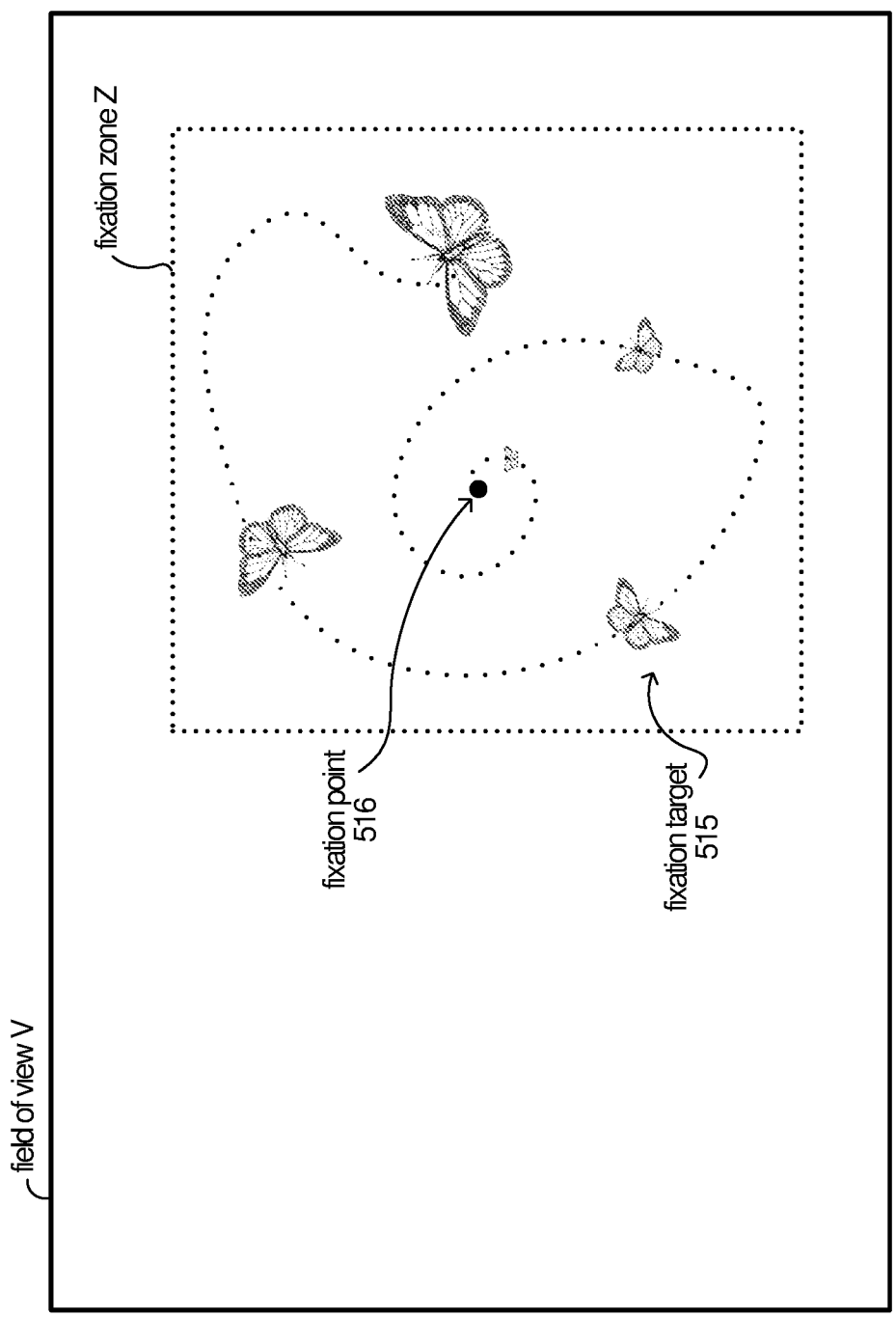
FIG. 5 depicts progression of another example animated fixation target within a fixation zone of a viewing area for guiding or steering an examinee's line of sight toward alignment for fundus imaging, according to some implementations.
Figure 6C:
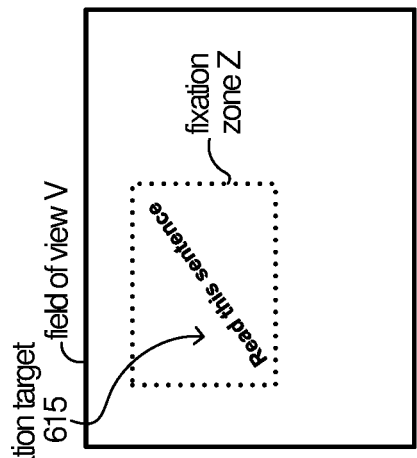
FIGS. 6A, 6B, 6C, 6D, 6E and 6F depict progression of another example animated fixation target within a fixation zone of a viewing area for guiding or steering an examinee's line of sight toward alignment for fundus imaging, according to some implementations.
Figure 6F:
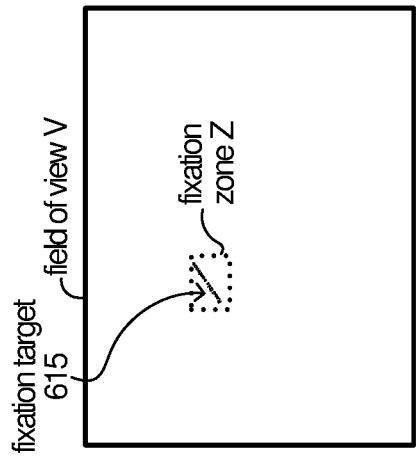
Figure 6B:
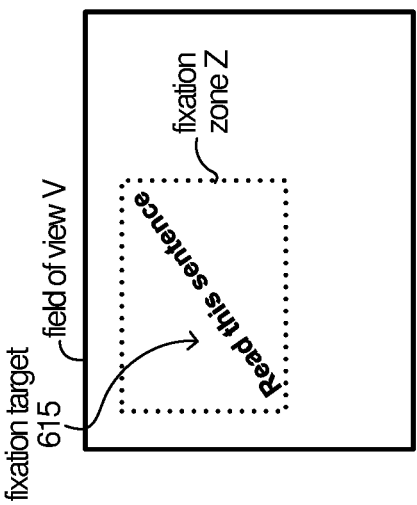
Figure 6E:
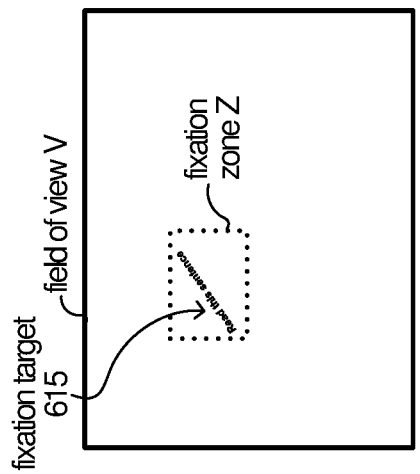
Figure 6A:
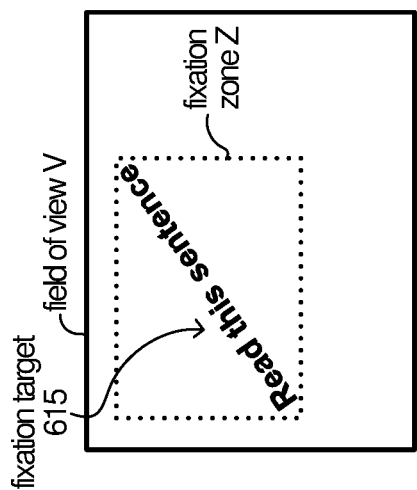
Figure 6D:
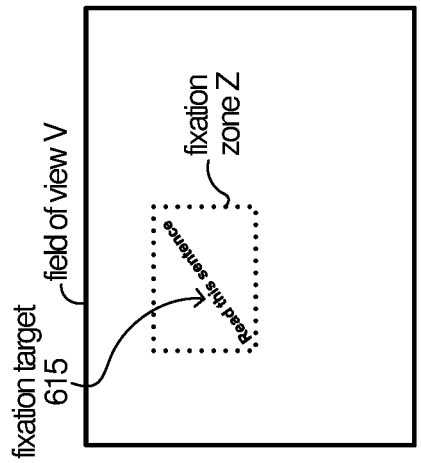

FIG. 5 depicts progression of another example animated fixation target 515 within a fixation zone Z of a viewing area V for guiding or steering an examinee's line of sight toward fixation alignment for fundus imaging, according to some implementations.

As discussed herein, traditional fundus cameras use a fixation point (or dot) and ask the examinee to stare at the fixation point as intently as possible. However, an examinee can only maintain his or her gaze for so long. As shown in the example of FIG. 5, an animated fixation target 515 is shown to the examinee in a dimly lit fixation window or area. The examinee is asked to look in the fixation zone Z, e.g., window or box. Advantageously, the fixation zone Z is relatively large compared to the dot used by traditional fundus cameras.

As shown in the example of FIG. 5, the animated fixation target (or image) 515 is a butterfly, e.g., flapping its wings as it flies around fixation zone Z. The examinee is asked to follow the trajectory of the animated fixation target 515 as it flies around the fixation zone Z and slowing shrinks to a fixation point 516 where the image stops. As soon as the image stops, the examinee's gaze is automatically drawn to that location, e.g., the fixation point, and the fundus camera images the eye.

FIGS. 6A-6F depict progression of another example animated fixation target 615 within a fixation zone Z of a viewing area V for guiding or steering an examinee's line of sight toward fixation alignment for fundus imaging, according to some implementations.

When an examinee is intently focused, their pupils tend to expand. Accordingly, the display can project a fixation target 615 with a word or very small sentence that gets smaller and smaller as it progresses to a fixation point. This process tends to increase fixation or focus because as the examinee reads along the sentence shrinks to a fixation point. At a certain point, the image will stop shrinking and the fundus camera images the eye as the examinee is focused as intently as possible to read the very small print word(s).

FIG. 6 further illustrates an example whereby the fixation zone Z gradually shrinks. In some implementations, the animated fixation target 615 and/or the fixation zone can gradually shrink causing the examinee to intently focus on a fixation point.

Figure 7:
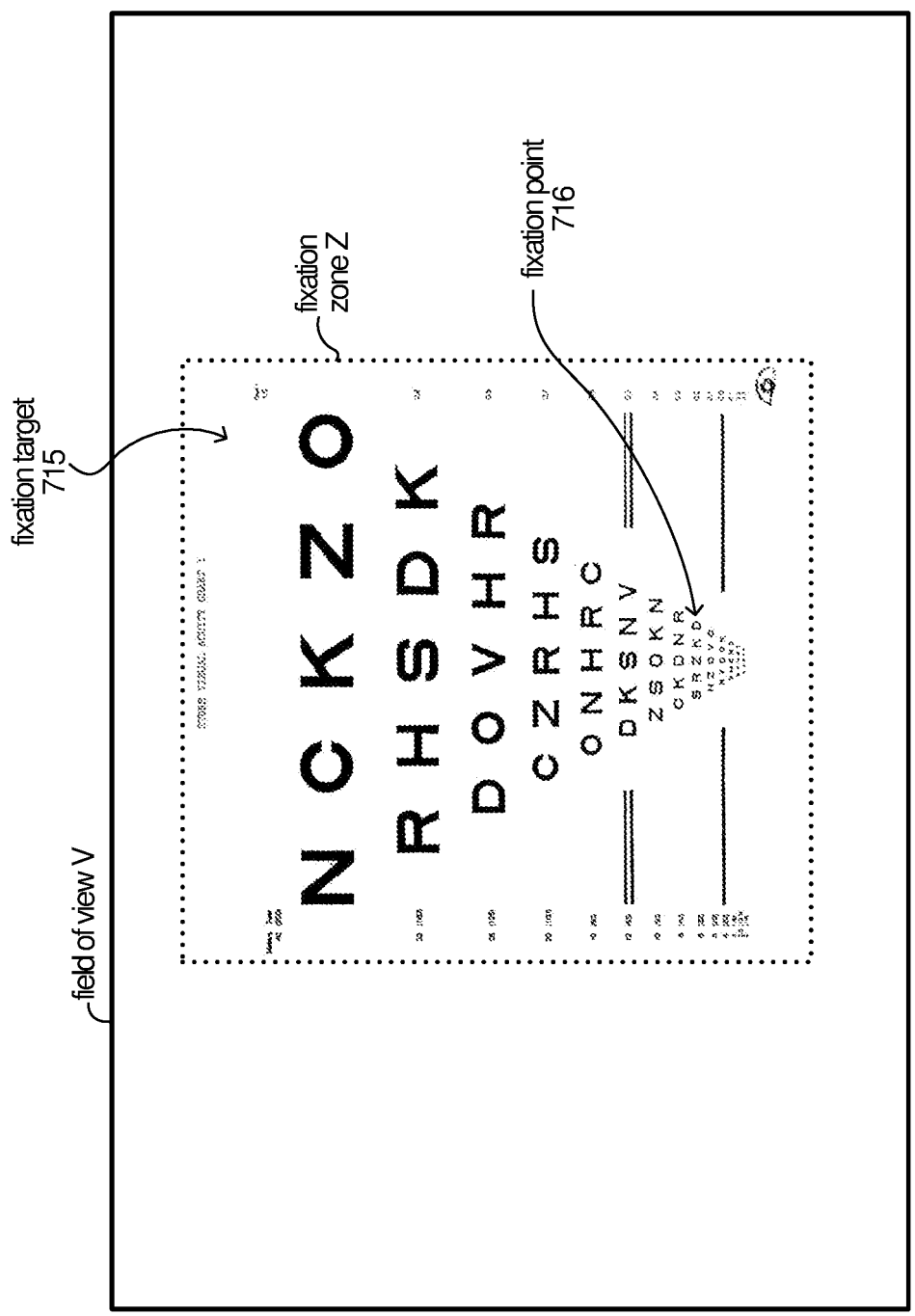
FIG. 7 depicts an example whereby an animated fixation target is a visual field or acuity test within a fixation zone of a viewing area for guiding or steering an examinee's line of sight toward alignment for fundus imaging, according to some implementations.

FIG. 7 depicts an example whereby an animated fixation target is a visual field or acuity test 715 within a fixation zone Z of viewing area V for guiding or steering an examinee's line of sight toward fixation alignment for fundus imaging, according to some implementations.

As discussed above, when an examinee is intently focused, their pupil tends to expand. In some implementations, the animated fixation target can be a visual field or acuity test. In such instances, the fixation target 715 could shrink to a fixation point. Alternatively, the examinee's line of sight can be tracked and the smallest readable print can be the fixation point. In the example of FIG. 7, the letter "D" comprises the fixation point.

In some implementations, the fundus camera can be used to conduct both the visual field or acuity test and the fundus imaging.

Figure 8:
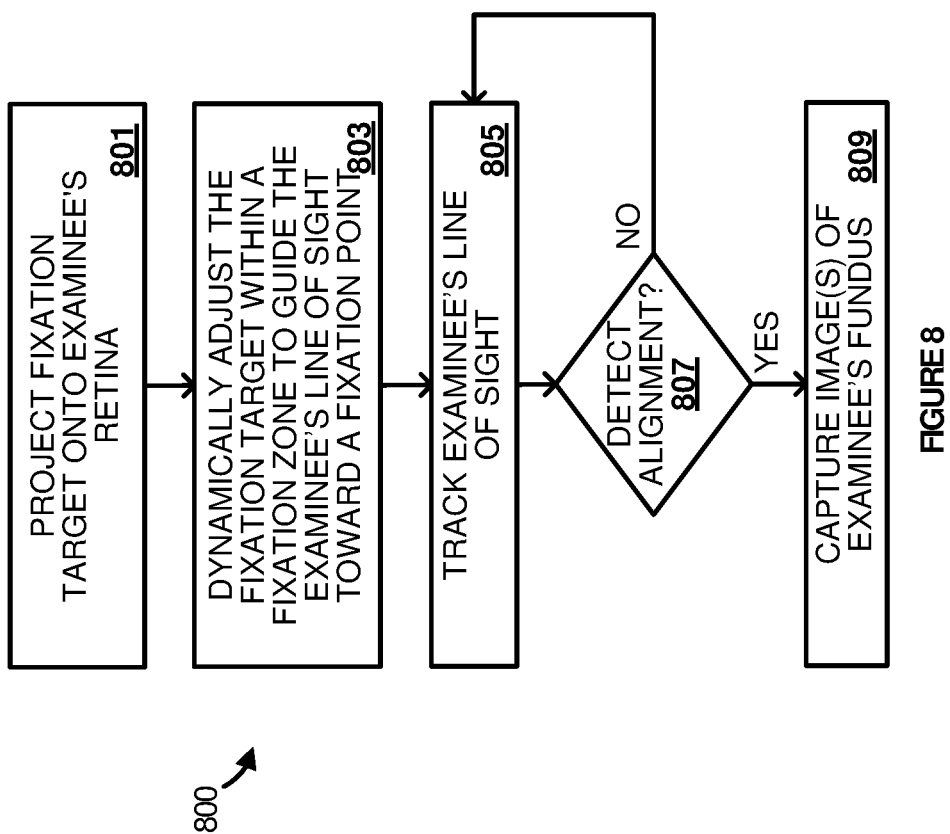
FIG. 8 depicts a flow diagram illustrating example operations of a fundus camera having a display, according to some implementations.

FIG. 8 depicts a flow diagram illustrating example operations 800 of a fundus camera having a display, according to some implementations. More specifically, the example of FIG. 8 depicts operations of a fundus camera having a display for projecting an animated fixation target onto an eye of an examinee for guiding or steering an examinee's line of sight toward fixation alignment for fundus imaging. The example operations 800 may be performed in various implementations by a fundus camera such as, for example, fundus camera 110a or 110b of FIG. 1A or FIG. 1B, respectively, or one or more processors, modules, engines, or components associated therewith.

To begin, at 801, the fundus camera projects a fixation target onto the examinee's eye, e.g., retina. At 803, the fundus camera dynamically adjusts the fixation target within a fixation zone to guide the examinee's line of sight toward a fixation point. At 805, the fundus camera tracks or monitors the examinee's line of sight. At decision 807, the fundus camera determines if fixation alignment is detected. If not, the fundus camera continues to track the examinee's line of sight. If so, at 809, the fundus camera automatically captures images of the examinees fundus.

Figure 9:
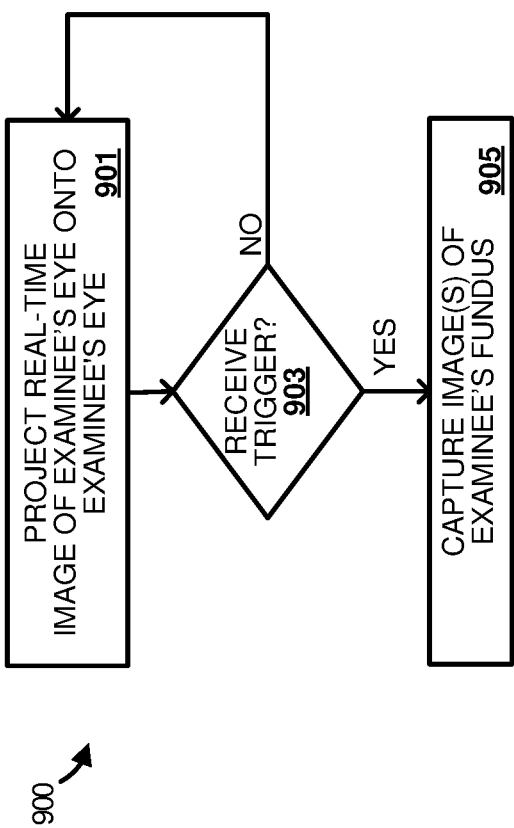
FIG. 9 depicts a flow diagram illustrating example operations of a fundus camera having a display, according to some implementations.

FIG. 9 depicts a flow diagram illustrating example operations 900 of a fundus camera having a display, according to some implementations. More specifically, the example of FIG. 9 depicts operations of a fundus camera having a display for projecting an animated fixation target onto an eye of an examinee for guiding or steering an examinee's line of sight toward fixation alignment for fundus imaging. The example operations 900 may be performed in various implementations by a fundus camera such as, for example, fundus camera 110a or 110b of FIG. 1A or FIG. 1B, respectively, or one or more processors, modules, engines, or components associated therewith.

To begin, at 901, the fundus camera projects a real-time video feed of the examinee's retina onto the examinee's retina. At decision 903, the fundus camera determines if a triggering event is received, e.g., via clicker. As discussed herein, in this implementation, the examinee can use the fundus camera in a "selfie-mode." If the triggering event is not detected, the fundus camera continues to project the real-time video feed. However, if the triggering event is received, at 905, the fundus camera directs the flash, captures images of the examinees fundus and stores the images in memory.

Figure 10:
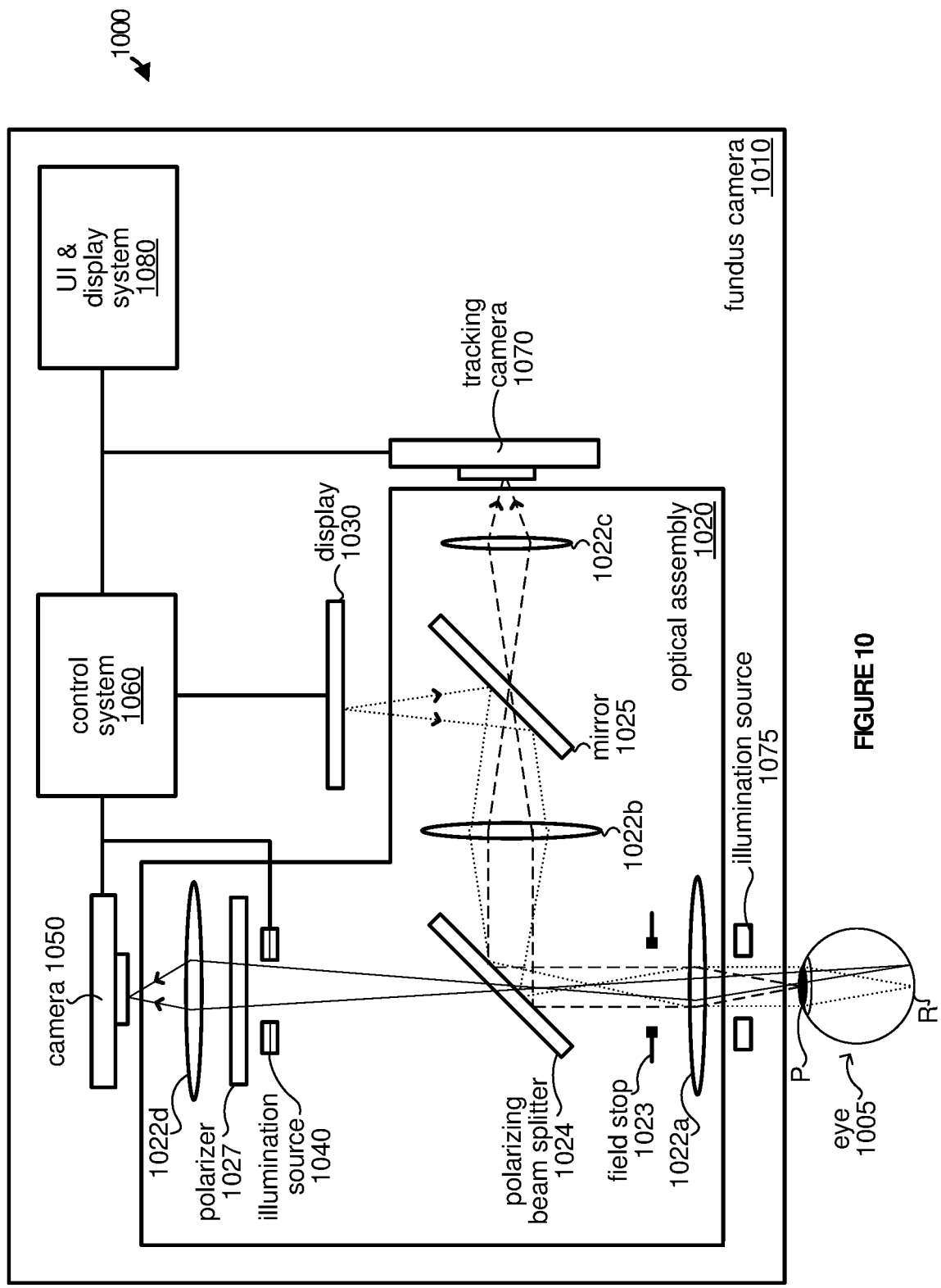
FIG. 10 depicts an example schematic architecture of a fundus camera including a visual feedback scheme for self-alignment, according to some implementations.

FIG. 10 depicts an example schematic architecture 1000 of a fundus camera 1010 including a visual feedback scheme for self-alignment, according to some implementations. As shown in the example of FIG. 10, the fundus camera includes a display 1030 that projects active visual alignment stimuli onto an eye 1005 of an examinee to facilitate pupil-to-camera alignment and/or fixation alignment for fundus photography.

The fundus camera 1010 includes optical assembly 1020, display 1030, infrared (IR) light emitting diode (LED) 1040, camera 1050, control system 1060, tracking camera 1070, illumination source 1075 and user interface (UI) and display system 1080. Additional or fewer components are possible.

As shown in the example of FIG. 10, the fundus camera 101 includes three imaging paths. The first imaging path illustrates projection of active visual alignment stimuli from display 1030 onto an imaging eye 1005 of the examinee via one or more components of the optical assembly 1020. More specifically, the display 1030 projects active visual alignment stimuli onto mirror 1025 via lens 1022b which, in turn, projects the active visual alignment stimuli onto polarizing beam splitter 1024. The polarizing beam splitter 1024 projects the active visual alignment stimuli onto the retina R of eye 1005 via lens 1022a. The second imaging path illustrates tracking of a position of the eye 1005 by the tracking camera 1070. More specifically, the tracking camera 1070 tracks a position of the eye 1005 through lens 1022a, projected from polarizing beam splitter 1024, through lens 1022b, mirror 1025, and lens 1022c. Lastly, the third imaging path illustrates imaging the fundus by camera 1050 through lens 1022a, polarizing beam splitter 1024, polarizer 1027 and lens 1022d.

The optical assembly 1020 includes lenses 1022a-1022d, field stop 1023, polarizing beam splitter 1024, mirror 1025, and polarizer 1027. In some implementations, the fundus camera 1010 may be constructed in the form of a handheld device where an examinee holds the fundus camera in front of the eye and manually moves the device and/or his or her head for fundus imaging alignment. The handheld device can be a cylindrically-shaped optomechanical tube that an examinee can look through for self-imaging of the fundus. Alternatively, the fundus camera 1010 can be table-top or wall-mounted device, in which case the user can either adjust head position or use a mechanical stage to align the camera.

The illumination source 1040 can be any light source that emits illumination light and/or otherwise provides a light (or flash) for capturing fundus images via camera 1050. As shown in the example of FIG. 10, the illumination light is projected onto eye 1005 of the examinee by one or more components of optical assembly 1020. Camera 1050 can be any camera configured to capture images of the fundus via optical assembly 1020. In some implementations, camera 1050 can be a high-speed camera that enables multiple images or frames to be taken during an extended flash.

The display 1030 projects the visual alignment stimuli onto a retina R of an examinee's eye 1005 via one or more components of the optimal assembly 1020. The visual alignment stimuli can include an active alignment pattern that is dynamically adjusted relative to a reference alignment pattern based on axial and lateral positions, i.e., axial displacement and a two-dimensional lateral shift, of the eye to guide the examinee toward pupil-to-camera alignment. Alternatively or additionally, the visual alignment stimuli can include an animated fixation target that is that is dynamically adjusted within a fixation zone to facilitate dilation of pupil P while guiding or steering the examinee toward fixation alignment. Various combinations or variations of the visual alignment stimuli are also possible.

Display 1030 can be any small, high-resolution electronic display, e.g., OLED, LCD, display with micromirrors on glass or silicon with the ability to provide high contrast and color, etc., designed for use in near-eye applications. As shown in the example of FIG. 10, the display 1030 is placed at the conjugate plane of the retina R to visually guide the examinee toward alignment. In some implementations, display 130 can be a microdisplay or have a display panel that is two inches or less.

The control system 1060 is operably coupled with various components of fundus camera 1010 for providing control information to components and/or receiving feedback from the components. As shown in the example of FIG. 10, the control system 1060 is operably coupled with display 1030, illumination source 1040, camera 1050, tracking camera 1070, illumination source 1075 and UI & display system 1080. The tracking camera 1070 can provide the control system 1060 with eye tracking position information or feedback. The control system 1060 monitors the eye tracking position information or feedback and closes the feedback loop between the eye position and the active visual alignment stimuli. For example, control system 1060 can guide the examinee toward pupil-to-camera alignment and/or fixation alignment and determine when the pupil-to-camera alignment and/or the fixation alignment are achieved. In some implementations, control system 1060 can direct the illumination source 1040 to emit a flash and the camera 1050 to capture one or more images during the flash once the pupil-to-camera alignment and/or the fixation alignment are achieved.

The tracking camera 1070 can be any camera or apparatus operable to continuously track and/or monitor the position of the eye of the examinee via one or more components of optical assembly 1020. As shown in the example of FIG. 10, tracking camera 1070 is operably coupled with an illumination source 1075. As discussed herein, the fundus camera 1010 can use any technique for eye tracking that can measure both the axial and lateral position of the eye relative to fundus camera 1010, preferably with precision on the order of millimeters or better.

As noted above, various techniques for tracking the position of the eye of the examinee can be used. In some implementations, tracking camera 1070 can be an iris camera with the illumination source comprising infrared illumination. In such instances, the eye position can be determined using an image-assisted eye tracking technique. That is, the eye position can be measured from video taken with the iris camera by performing real-time object tracking of the pupil and/or corneal reflection spots. Using this technique, the center position of the pupil indicates lateral position of the eye and the relative positions of the corneal reflections spots indicate the axial position of the eye and the tilt of the pupil plane with respect to the illumination sources. However, as noted above, any eye tracking technique that can measure both the axial and lateral position of the eye relative to fundus camera 1010 can be utilized. For example, although not shown in the example of FIG. 10, in some implementations, instead of the tracking camera 1070, an IR illuminated retinal image or a direct camera view of the examinee's eye 1005 can be used to track the position of the eye.

As shown in the example of FIG. 10, the tracking camera 1070 provides feedback to the control system which, in turn, directs display 1030 to dynamically adjust the visual alignment stimuli. For example, to guide the examinee toward pupil-to-camera alignment an active alignment pattern can be adjusted relative to a reference alignment pattern based on the position of the eye of the examinee relative to the fundus camera. More specifically, the control system 1060 directs the display 1030 to guide the examinee toward alignment by dynamically adjusting the active alignment pattern relative to the reference alignment pattern based on the position of the eye of the examinee relative to the fundus camera. As discussed herein, the tracking camera 1070 monitors the position of the eye of the examinee in real-time (or near real-time). In some implementations, the tracking camera 1070 is operable to track the position of the eye of the examinee at a frame rate greater than ~10 fps in order to provide the real-time (or near real-time) tracking.

FIGS. 11A-11D depict example active visual alignment stimuli that are projected onto an eye of an examinee within a field of view V for guiding or steering the examinee's line of sight toward pupil-to-camera alignment, according to some implementations. More specifically, the examples of FIGS. 11A-11D illustrate an active alignment pattern 1110 projected on the eye of the examinee and adjusted in real-time (or near real-time), based on axial and lateral positions of the eye, relative to reference alignment pattern 1120 to guide or steer the examinee toward pupil-to-camera alignment.

As shown in the examples of FIGS. 11A-11D, the reference alignment pattern 1120 remains fixed at the center of the field of view V while the active alignment pattern 1110 moves and changes size with the position of the eye of the examinee relative to the camera. In some implementations, the size of the active alignment pattern 1110 indicates an axial displacement of the eye of the examinee relative to the fundus camera. For example, the active alignment pattern 1110 appears larger when the eye of the examinee is to far from the fundus camera and appears smaller when the eye of the examinee is too close to the fundus camera. Alternatively or additionally, colors can be used to indicate axial and/or lateral displacement.

In some implementations, the examinee is instructed to move the camera or his or her head to match the active alignment pattern 1110 to the reference alignment pattern 1120 in size and position. As noted above, the fundus camera dynamically moves or adjusts the active alignment pattern 1110 to the reference alignment pattern 1120 based on this movement. Pupil-to-camera alignment is achieved when the active alignment pattern 1110 and the reference alignment pattern 1120 overlap or fit together in a predetermined manner on the display. For example, as shown in the examples of FIGS. 11A-11D, the active alignment pattern 1110 is a circle and the reference alignment pattern 1120 is a cross and the user is instructed to move the camera or his or her head to match the circle and the cross.

In some implementations, once aligned, the camera automatically flashes and captures one or more images of the fundus. The examples of FIGS. 11A-11C illustrates the process of guiding or steering the examinee toward pupil-to-camera alignment. Referring first to FIG. 11A, the eye of the examinee is off-center laterally and too far from the fundus camera axially. In FIG. 11B, the eye of the examinee is off-center laterally and too close to the fundus camera axially. Likewise, in FIG. 11C, the eye of the examinee is centered laterally but too far from the fundus camera axially. Lastly, FIG. 11D illustrates the active alignment pattern 1110 and the reference alignment pattern 1120 overlapped or otherwise fitting together in a predetermined manner for alignment.

It is appreciated that any pair of objects where one is static relative to the other can be used in the examples of FIGS. 11A-11D. Alternatively, arrows or other indicators can be used that indicate the direction and amount in which to move. Color and sizes of the patterns can be changed as well to indicate that the alignment is correct or to provide other signals/instructions. Moreover, since this active alignment stimuli is projected at the infinity to the eye, in some implementations, the stimuli can also serve as a fixation point for the examinee. Likewise, the location of the fixation point in the display plane can be shifted to guide the examinee so that the camera, e.g., camera 1050, can image different regions of the retina.

FIG. 12 depicts a flow diagram illustrating example operations 1200 of a fundus camera having a display operable to project active visual alignment stimuli, according to some implementations. More specifically, the example of FIG. 12 depicts operations 1200 of a fundus camera having a display for projecting active visual alignment stimuli to facilitate pupil-to-camera alignment and fixation alignment. The example operations 1200 may be performed in various implementations by a fundus camera such as, for example, fundus camera 1010 of FIG. 10, or one or more processors, modules, engines, or components associated therewith.

To begin, at 1201, the fundus camera adjusts an active alignment pattern relative to the reference alignment pattern based on a position of the eye of the examinee relative to the fundus camera. At decision 1203, the fundus camera determines if pupil-to-camera (or eyebox) alignment is achieved. If not, the fundus camera continues adjusting the active alignment pattern relative to the reference alignment pattern at 1201. Otherwise, if pupil-to-camera alignment is achieved, at 1205, the fundus camera dynamically adjusts the animated fixation target within a fixation zone for facilitating dilation of a pupil of the eye while guiding the examinee's line of sight toward fixation alignment. At decision 1207, the fundus camera determines if pupil-to-camera (or eyebox) alignment is achieved. If not, the fundus camera continues adjusting the animated fixation target within the fixation zone at 1205. Otherwise, if fixation alignment is achieved, at 1209, the fundus camera captures one or more images of the examinee's fundus and/or notifies or indicates that optical alignment is successful.

Figure 13A:
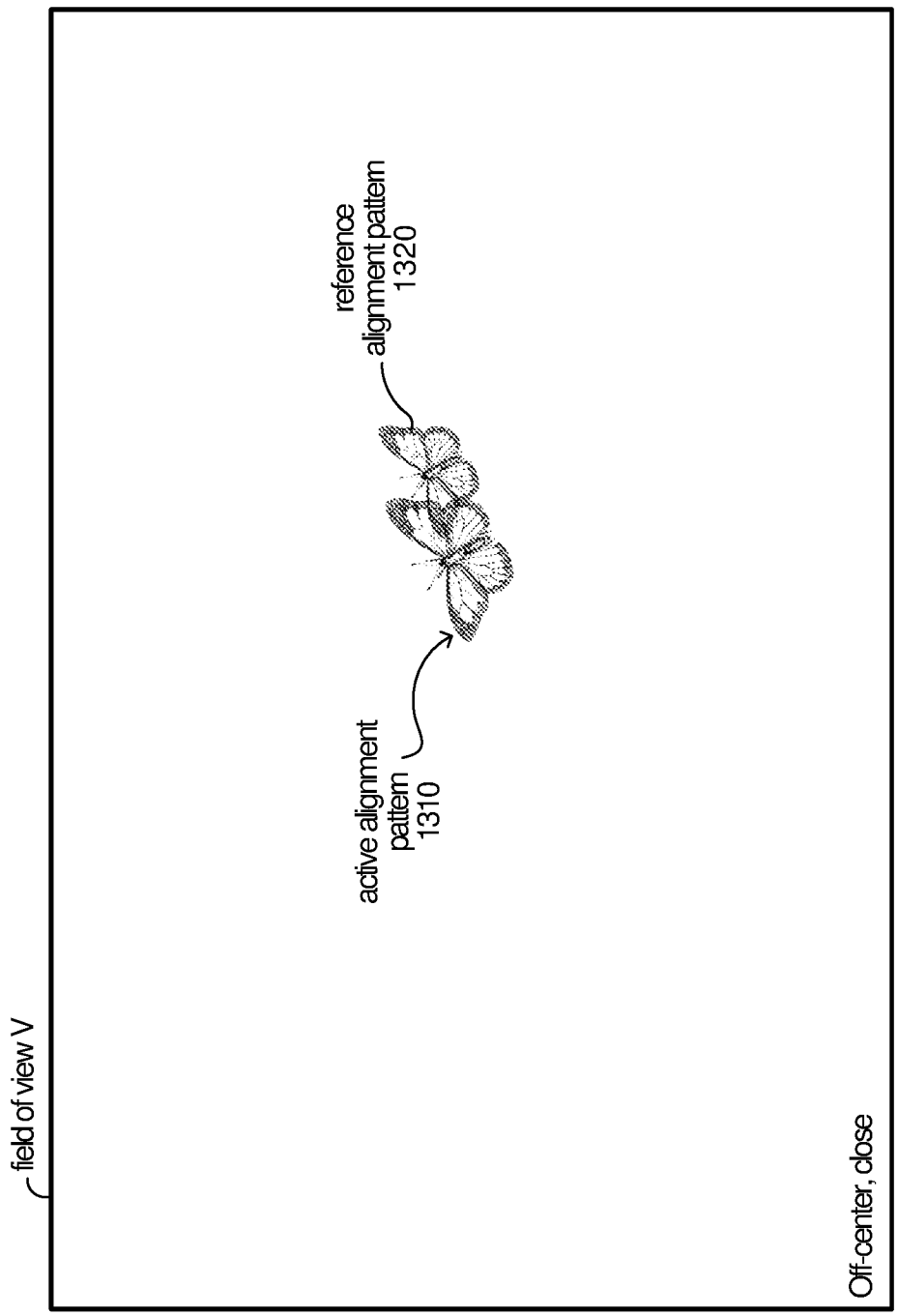
FIGS. 13A and 13B depict example active visual alignment stimuli that are successively projected onto an eye of an examinee within a field of view for guiding or steering the examinee's line of sight toward pupil alignment, according to some implementations.
Figure 13B:
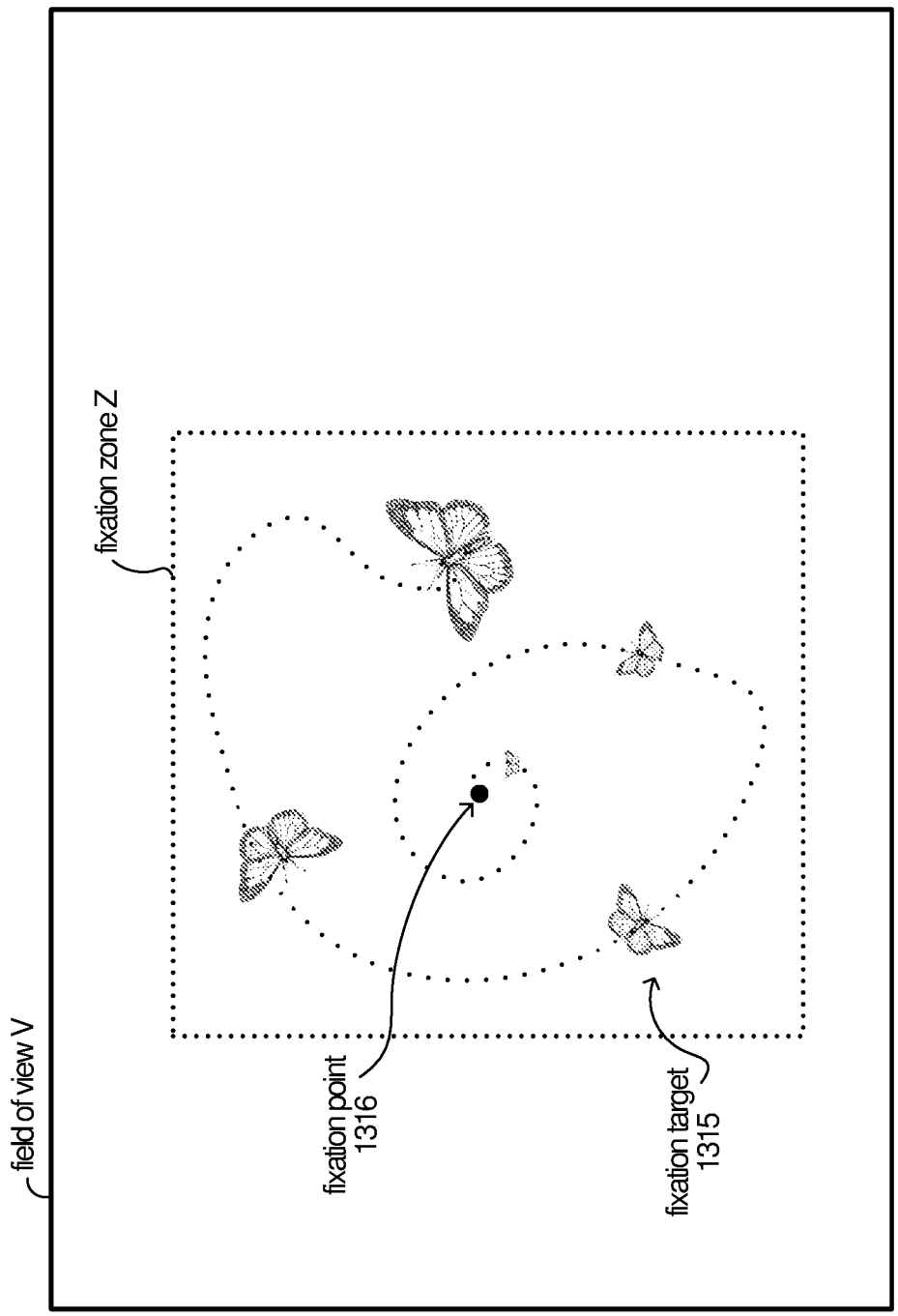

FIGS. 13A and 13B depict example active visual alignment stimuli that are successively projected onto an eye of an examinee within a field of view V for guiding or steering the examinee's line of sight toward pupil alignment, according to some implementations. More specifically, FIGS. 13A and 13B illustrate active visual alignment stimuli that are successively projected onto an eye of an examinee for achieving pupil-to-camera alignment (FIG. 13A) followed by fixation alignment (FIG. 13B).

Referring first to FIG. 13A, FIG. 13A depicts active visual alignment stimuli including active alignment pattern 1310 and reference alignment pattern 1320. As shown in the examples of FIGS. 13A and 13B, the active alignment pattern 1310 and a reference alignment pattern 1320 are images of butterflies. The images of butterflies can be static or can appear to be moving (even while remaining in the same position), e.g., by flapping wings, etc.

As noted above, the fundus camera monitors or tracks the position of the eye of the examinee in real-time (or near real-time) to guide or steer the examinee toward pupil-to-camera alignment by dynamically adjusting the active alignment pattern 1310 in real-time (or near real-time) relative to the reference alignment pattern 1320 based on the position of the eye of the examinee relative to the fundus camera.

When the active alignment pattern 1310 and the reference alignment pattern 1320 match or overlap, pupil-to-camera alignment is achieved. At this point, fixation alignment occurs as illustrated in the example in FIG. 13B and the active alignment pattern 1310 and the reference alignment pattern 1320 become a single animated fixation target 1315.

FIG. 13B depicts progression of the animated fixation target 1315 within a fixation zone Z of a viewing area V for guiding or steering an examinee toward fixation alignment. The fixation alignment technique discussed herein improves fixation and facilitates dilation of a pupil of the eye of the examinee for fundus imaging.

As discussed herein, traditional fundus cameras use a fixation point (or dot) and ask the examinee to stare at the fixation point as intently as possible. However, an examinee can only maintain his or her gaze for so long. As shown in the example of FIG. 13B, animated fixation target 1315 is shown to the examinee in a dimly lit fixation window or area. The examinee is asked to look in the fixation zone Z, e.g., window or box. Advantageously, the fixation zone Z is relatively large compared to the dot used by traditional fundus cameras.

As shown in the example of FIG. 13B, the animated fixation target (or image) 1315 is a butterfly, e.g., flapping its wings as it flies around fixation zone Z. The examinee is asked to follow the trajectory of the animated fixation target 1315 as it flies around the fixation zone Z and slowing shrinks to a fixation point 1316 where the image stops. As soon as the image stops, the examinee's gaze is automatically drawn to that location, e.g., the fixation point, and the fundus camera images the eye.

The fundus camera can select the location of the fixation point 1316 in order to image a particular region of the retina. Although not shown, the process of FIG. 13B can be repeated (or cycled through) for imaging multiple different regions of the retina, e.g., by selecting different fixation points.

Figure 14:
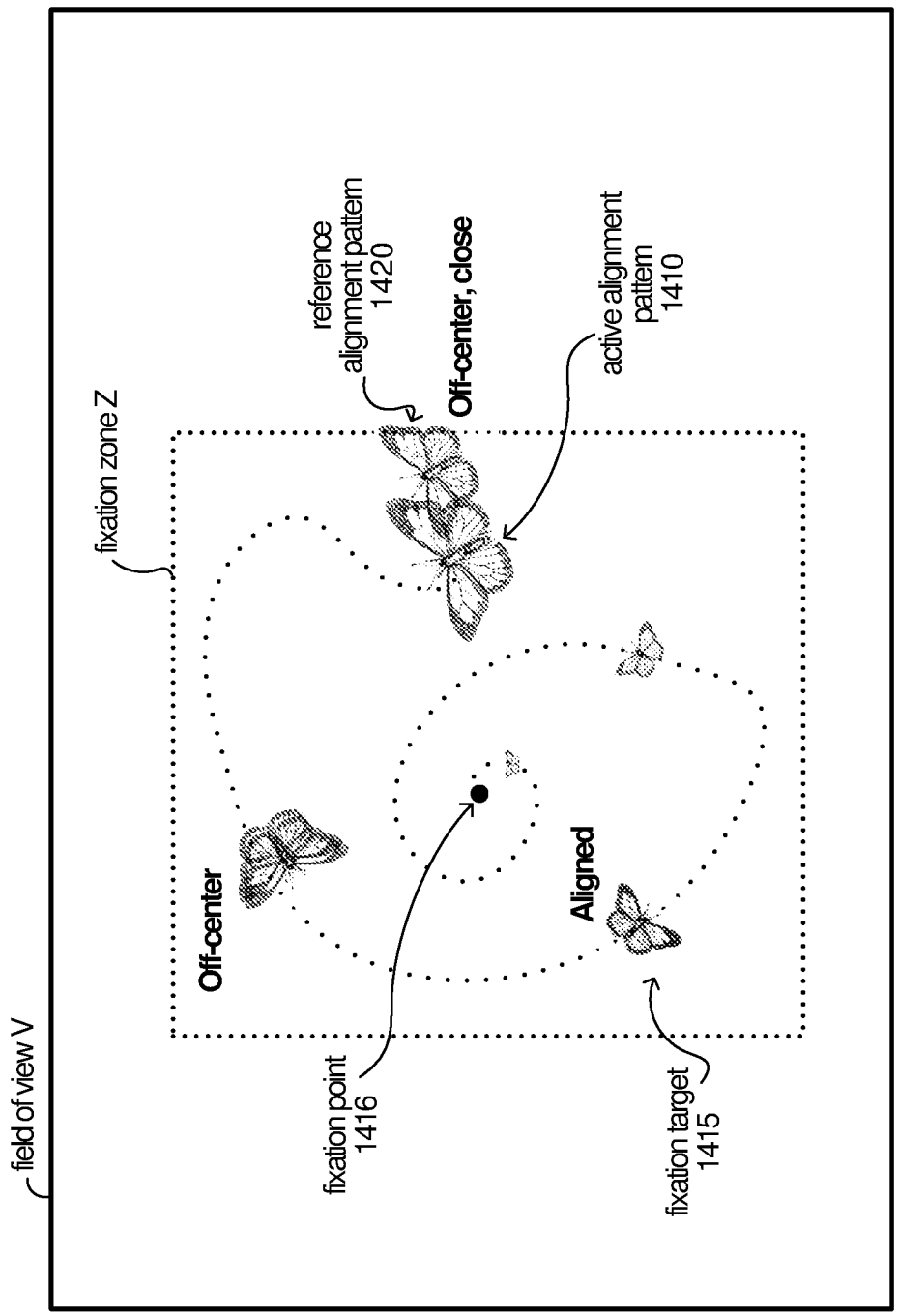
FIG. 14 depicts example active visual alignment stimuli that are projected onto an eye of an examinee within a field of view for guiding or steering the examinee's line of sight toward optical alignment, according to some implementations.

FIG. 14 depicts example active visual alignment stimuli that are projected onto an eye of an examinee within a field of view V for guiding or steering the examinee's line of sight toward optical alignment, according to some implementations. The example of FIG. 14 is similar to the examples of FIGS. 13A and 13B, however, the pupil-to-camera and angular alignment occur concurrently.

Figure 15:
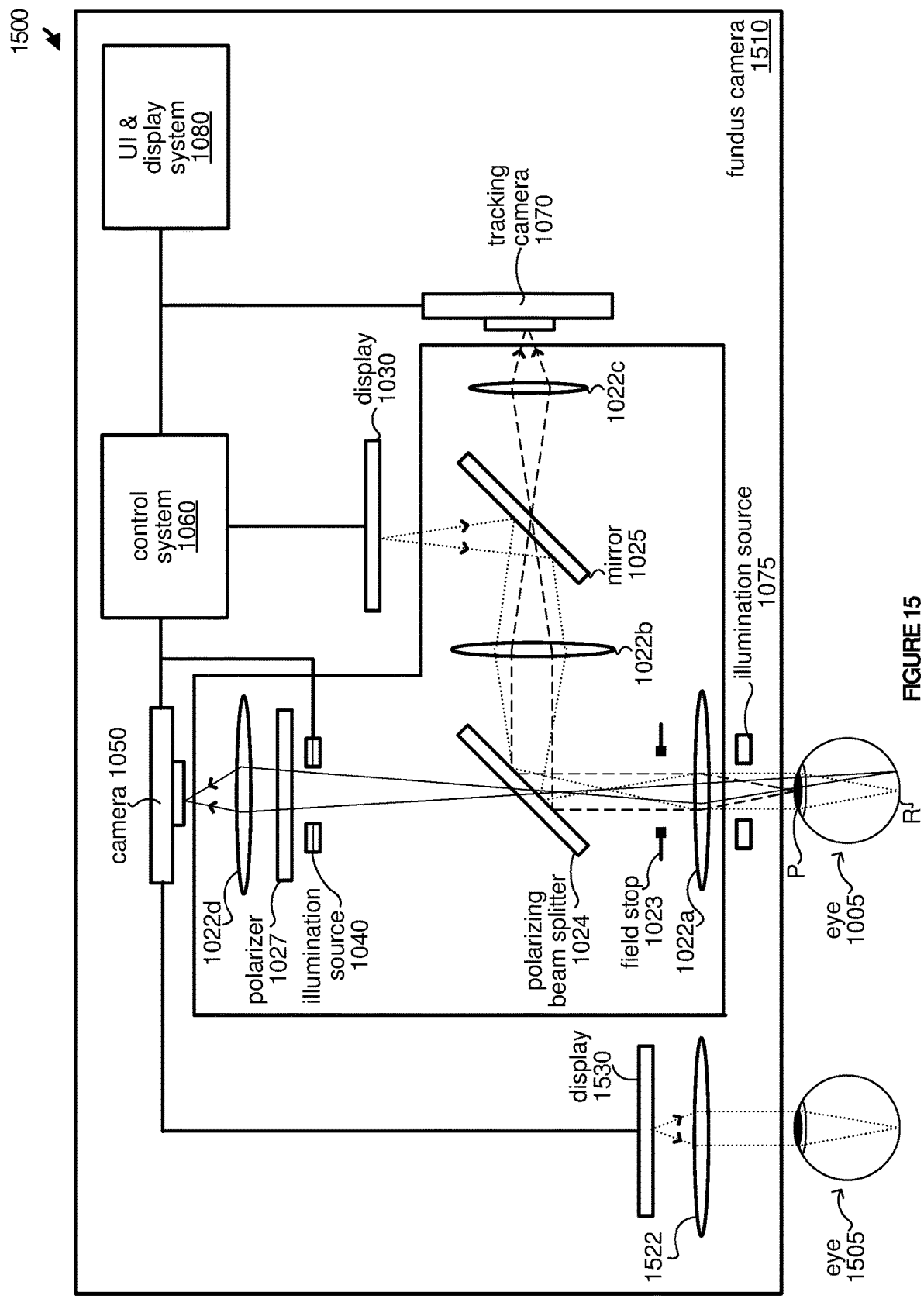
FIG. 15 depicts an example schematic architecture of a fundus camera including a three-dimensional (3D) visual feedback scheme for self-alignment, according to some implementations.

FIG. 15 depicts an example schematic architecture 1500 of a fundus camera 1510 including a three-dimensional (3D) visual feedback scheme for self-alignment, according to some implementations. As shown in the example of FIG. 15, active visual alignment stimuli can be displayed both on the imaging eye 1005 and the non-imaging eye 1505 in a non pupil-forming display scheme similar to a virtual reality (VR) headset by placing the active visual alignment stimuli one focal distance away from an eyepiece (not shown). The fundus camera 1510 includes components of fundus camera 1010 of FIG. 10 but also includes an additional display 1530 and lens 1522 for projecting active visual alignment stimuli onto a non-imaging eye 1505. The lens 1522 can be a low-quality lens.

Fundus camera 1510 can achieve precise 3D alignment of imaging eye's 1005 pupil with respect to the eye box of the camera using a stereo display projected to both eyes (imaging and non-imaging eye). The operation of fundus camera 1510 is discussed with reference to FIG. 16 which illustrates left and right displays that are separately projected onto the imaging and non-imaging eye of the examinee.

In some implementations, the left and right displays include two image objects: one static object 1620 and one active object 1610 which moves with the position of the examinee's imaging eye. Based on binocular disparity, each display (left and right) will be rendered to show the static object 1620 at a fixed point in virtual 3D space while the active object 1610 moves in virtual 3D space with the measured 3D position of the imaging eye 1005. When the imaging eye 1005 is aligned to the eyebox of the camera, the objects are displayed on the same pixel position of the display screen and the examinee perceive the virtual objects in the same position on the virtual 3D space.

Figure 16A:
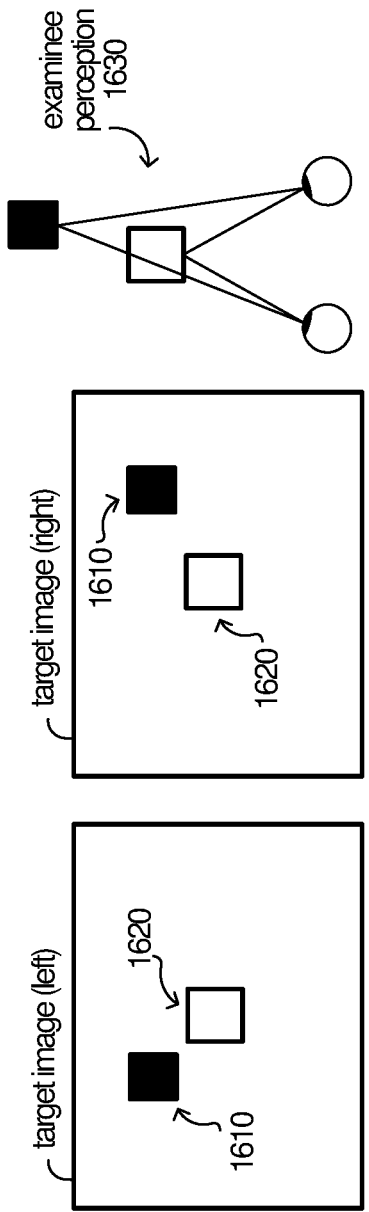
FIGS. 16A and 16B depict example depth alignment schemes using a 3D display in the case when the eye is too far from and to close to the fundus camera, respectively, according to some implementations.
Figure 16B:
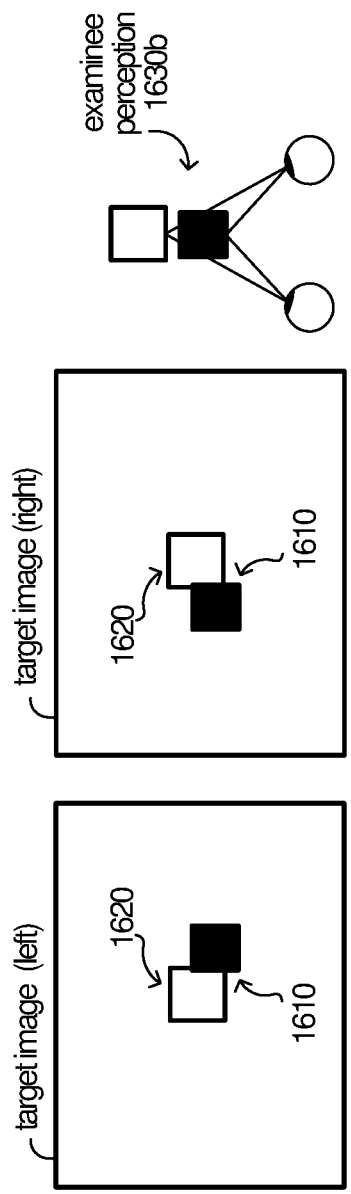

The examples of FIGS. 16A and 16B depict a depth alignment scheme using 3D display in the case when the eye is too far from and to close to the fundus camera, respectively. In some implementations, the 3D display scheme provides a more immersive self-imaging experience than monocular alignment scheme.

Certain inventive aspects may be appreciated from the foregoing disclosure, of which the following are various examples.

Example 1. A fundus camera comprising: an optical assembly including one or more optical components; a display adapted to project an animated fixation target onto an eye of an examinee via the optical assembly; an illumination source adapted to emit one or more flashes onto the eye of the examinee via the optical assembly; a camera adapted to capture multiple images of the examinee's fundus during the one or more flashes; and a control system operably coupled with the display, the illumination source and the camera, and configured to direct the display to dynamically adjust the animated fixation target within a fixation zone for facilitating dilation of a pupil of the eye while guiding the examinee's line of sight toward fixation alignment.

Example 2. The fundus camera of example 1, wherein to dynamically adjust the animated fixation target within the fixation zone, the control system is configured to direct the display to progressively shrink the animated fixation target until the animated fixation target becomes a fixation point.

Example 3. The fundus camera of example 1, wherein to dynamically adjust the animated fixation target within the fixation zone, the control system is configured to direct the display to progressively shrink the fixation zone until the fixation zone becomes a fixation point.

Example 4. The fundus camera of example 3, wherein to progressively shrink the fixation zone, the control system is configured to maintain a relative position of the animated fixation target within the fixation zone.

Example 5. The fundus camera of example 1, wherein the animated fixation target comprises one or more of an image, a video, or one or more words, letters or numbers.

Example 6. The fundus camera of example 1, wherein the animated fixation target comprises a visual field or acuity test.

Example 7. The fundus camera of example 1, wherein the control system is configured to direct the display to project the animated fixation target for a preset duration, and wherein the animated fixation target comprises one or more preset animations.

Example 8. The fundus camera of example 1, wherein the control system is configured to direct the display to adjust ambient lighting conditions during the fixation alignment.

Example 9. The fundus camera of example 1, wherein the control system is adapted to receive a real-time video feed from the camera and direct the display to project the real-time video feed onto the eye of the examinee.

Example 10. The fundus camera of example 1, further comprising: an eye tracker adapted to monitor the eye of the examinee while the control system directs the display to dynamically adjust, based on an output of the eye tracker, the animated fixation target within the fixation zone.

Example 11. The fundus camera of example 10, wherein to monitor the eye of the examinee, the eye tracker is adapted to track a location or size of the examinee's pupil, and wherein the control system directs the display to dynamically adjust, based on the location or size of the examinee's pupil, the animated fixation target within the fixation zone.

Example 12. The fundus camera of example 10, wherein the eye tracker comprises an iris camera and an infrared illumination source positioned to illuminate the examinee's eye.

Example 13. The fundus camera of example 10, wherein the control system is configured to determine that the fixation alignment is achieved based on the output of the eye tracker.

Example 14. The fundus camera of example 13, wherein the control system triggers, responsive to the determination that the fixation alignment is achieved, the illumination source to emit the one or more flashes and the camera to capture the multiple images of the examinee's fundus.

Example 15. The fundus camera of example 10, wherein the output of the eye tracker comprises a real-time video feed, and control system is configured to direct the display to project the real-time video feed onto the eye of the examinee.

Example 16. The fundus camera of example 15, further comprising: a trigger mechanism adapted to receive an input from the examinee, and wherein the control system is configured to direct the camera to capture the multiple images of the examinee's fundus responsive to receiving the input.

Example 17. The fundus camera of example 1, wherein the control system is configured to direct the display to project one or more camera state indicators onto the eye of the examinee.

Example 18. The fundus camera of example 1, wherein the display is situated within the image path at a conjugate plane of a retina.

Example 19. A fundus camera comprising: an optical assembly including one or more optical components; a display adapted to project an animated fixation target via the optical assembly; an eye tracker adapted to monitor an eye of an examinee; and a control system operably coupled with the display and the eye tracker, and configured to direct the display to dynamically adjust the animated fixation target within a fixation zone based on an output of the eye tracker to dilate a pupil of the eye while guiding the examinee's line of sight toward fixation alignment.

Example 20. The fundus camera of example 19, further comprising: an illumination source adapted to emit one or more flashes; and a camera adapted to capture multiple images of the examinee's fundus during the one or more flashes.

Example 21. The fundus camera of example 19, wherein to monitor the eye of the examinee, the eye tracker is adapted to track a location or size of the examinee's pupil.

Example 22. The fundus camera of example 21, wherein the control system is configured to continuously monitor, via an eye tracker, a degree or measure of alignment.

Example 23. The fundus camera of example 22, wherein the control system is configured to determine that alignment is achieved when the degree or measure of alignment exceeds a predetermined threshold.

Example 24. The fundus camera of example 22, wherein the control system is configured to dynamically adjust the animated fixation target within the fixation zone based on the degree or measure of alignment.

Example 25. A method comprising: projecting an animated fixation target onto the eye of the examinee; dynamically adjusting the animated fixation target within a fixation zone to dilate the pupil of the eye while guiding the examinee's line of sight toward fixation alignment; and capturing one or more images of the examinee's fundus.

Example 26. The method of example 25, further comprising: tracking the eye of the examinee while dynamically adjusting the animated fixation target within the fixation zone, wherein the animated fixation target is dynamically adjusted based on the tracking.

Example 27. The method of example 26, wherein tracking the eye of the examinee comprises obtaining tracking information including location or size of the examinee's pupil.

Example 28. The method of example 27, further comprising: determining when alignment is achieved based on the tracking information.

Example 29. The method of example 28, further comprising: automatically triggering the capturing of the image of the examinee's fundus in response to the determination that the fixation alignment is achieved.

Example 30. A fundus camera comprising: an optical assembly including one or more optical components; a display adapted to project an active alignment pattern and a reference alignment pattern onto an eye of an examinee via the optical assembly; a camera adapted to capture one or more images of the examinee's fundus; an eye tracker adapted to monitor a position of the eye of the examinee relative to the fundus camera; and a control system operably coupled with the display, the camera, and the eye tracker, and configured to direct the display to guide the examinee toward pupil-to-camera alignment by dynamically adjusting the active alignment pattern relative to the reference alignment pattern based on the position of the eye of the examinee relative to the fundus camera.

Example 31. The fundus camera of example 30, wherein the position the eye tracker is adapted to monitor comprises an axial displacement and a two-dimensional lateral shift of the eye of the examinee relative to the fundus camera.

Example 32. The fundus camera of example 31, wherein the eye tracker comprises an iris camera and an infrared illumination source positioned to illuminate the examinee's eye.

Example 33. The fundus camera of example 31, wherein control system is configured to dynamically adjust a size of the active alignment pattern to visually indicate the axial displacement of the eye of the examinee relative to the fundus camera.

Example 34. The fundus camera of example 31, and wherein control system is configured to dynamically adjust a two-dimensional position of the active alignment pattern on the display to visually indicate the two-dimensional lateral shift of the eye of the examinee relative to the fundus camera.

Example 35. The fundus camera of example 31, wherein control system is adapted to dynamically adjust a color of the active alignment pattern to visually indicate the axial displacement or the two-dimensional lateral shift of the eye of the examinee relative to the fundus camera.

Example 36. The fundus camera of example 31, wherein the control system is configured to: monitor the axial displacement and the two-dimensional lateral shift of the eye of the examinee relative to the fundus camera to determine when pupil-to-camera alignment is achieved, wherein the active alignment pattern and the reference alignment pattern visually match in size and position on the display when the pupil-to-camera alignment is achieved.

Example 37. The fundus camera of example 36, wherein to match in size and position on the display, the active alignment pattern and the reference alignment pattern overlap or fit together in a predetermined manner.

Example 38. The fundus camera of example 36, wherein the reference alignment pattern comprises a cross, the active alignment pattern comprises a circle, and the active alignment pattern and the reference alignment pattern visually match in size and position when the edges of the cross are adjacent to a perimeter of the circle.

Example 39. The fundus camera of example 36, wherein the control system is configured to trigger an illumination source to emit one or more flashes and the camera to capture the one or more images of the examinee's fundus responsive to the determination that the pupil-to-camera alignment is achieved.

Example 40. The fundus camera of example 30, wherein the reference alignment pattern comprises a fixation target in a fixation zone.

Example 41. The fundus camera of example 40, wherein the control system is configured to direct the display to project the reference alignment pattern at various locations, and wherein each location corresponds to a different region of the examinee's fundus.

Example 42. The fundus camera of example 41, wherein the control system is configured to cycle through the various locations to capture one or more images of the examinee's fundus at each corresponding region.

Example 43. The fundus camera of example 30, wherein the control system is configured to direct the display to dynamically adjust an animated fixation target within a fixation zone for facilitating dilation of a pupil of the eye while guiding the examinee's line of sight toward fixation alignment.

Example 44. The fundus camera of example 43, wherein pupil-to-camera alignment is achieved prior to dynamically adjusting the animated fixation target within the fixation zone for facilitating dilation of the pupil of the eye while guiding the examinee's line of sight toward the fixation alignment.

Example 45. The fundus camera of example 44, wherein the reference alignment pattern becomes the animated fixation target when the pupil-to-camera alignment is achieved.

Example 46. The fundus camera of example 43, wherein pupil-to-camera alignment is achieved concurrently with dynamically adjusting the animated fixation target within the fixation zone for facilitating dilation of the pupil of the eye while guiding the examinee's line of sight toward the fixation alignment.

Example 47. The fundus camera of example 46, wherein the active alignment pattern and the reference alignment pattern collectively comprise the animated fixation target and combine into a single pattern when the pupil-to-camera alignment is achieved.

Example 48. The fundus camera of example 30, further comprising: a second display adapted to project the active alignment pattern and the reference alignment pattern onto a non-imaging eye of the examinee via the optical assembly, wherein the display and the second display are adapted to render the active alignment pattern and the reference alignment pattern in three-dimensional space based on binocular disparity.

Example 49. A fundus camera comprising: an optical assembly including one or more optical components; a display adapted to project visual alignment stimuli onto an eye of an examinee via the optical assembly; an illumination source adapted to emit one or more flashes onto the eye of an examinee via the optical assembly; a camera adapted to capture multiple images of the examinee's fundus during the one or more flashes; an eye tracker adapted to monitor the position of the eye of the examinee relative to the fundus camera; and a control system operably coupled with the display, the illumination source, the camera and the eye tracker, and adapted to direct the display to dynamically adjust the visual alignment stimuli including: adjusting an active alignment pattern relative to a reference alignment pattern based on a position of the eye of the examinee relative to the fundus camera; and adjusting an animated fixation target within a fixation zone for facilitating dilation of a pupil of the eye while guiding the examinee's line of sight toward fixation alignment.

Example 50. The fundus camera of example 49, wherein the position the eye tracker is adapted to monitor comprises an axial displacement and a two-dimensional lateral shift of the eye of the examinee relative to the fundus camera.

The functional block diagrams, operational scenarios and sequences, and flow diagrams provided in the Figures are representative of exemplary systems, environments, and methodologies for performing novel aspects of the disclosure. While, for purposes of simplicity of explanation, methods included herein may be in the form of a functional diagram, operational scenario or sequence, or flow diagram, and may be described as a series of acts, it is to be understood and appreciated that the methods are not limited by the order of acts, as some acts may, in accordance therewith, occur in a different order and/or concurrently with other acts from that shown and described herein. For example, those skilled in the art will understand and appreciate that a method could alternatively be represented as a series of interrelated states or events, such as in a state diagram. Moreover, not all acts illustrated in a methodology may be required for a novel implementation.

The descriptions and figures included herein depict specific implementations to teach those skilled in the art how to make and use the best option. For the purpose of teaching inventive principles, some conventional aspects have been simplified or omitted. Those skilled in the art will appreciate variations from these implementations that fall within the scope of the invention. Those skilled in the art will also appreciate that the features described above can be combined in various ways to form multiple implementations. As a result, the invention is not limited to the specific implementations described above, but only by the claims and their equivalents.

The invention claimed is:

1. A method of operating a fundus camera comprising:
projecting an animated fixation target onto an eye of an examinee via an optical assembly, wherein the animated fixation target comprises a continuously moving animation;
emitting one or more flashes onto the eye of the examinee via the optical assembly;
capturing, with the fundus camera, one or more images of the examinee's fundus during the one or more flashes; and
dynamically adjusting the animated fixation target within a fixation zone for facilitating dilation of a pupil of the eye while guiding the examinee's line of sight toward fixation alignment.

2. The method of claim 1, wherein dynamically adjusting the animated fixation target within the fixation zone comprises progressively shrinking the animated fixation target until the animated fixation target becomes a fixation point.

3. The method of claim 1, wherein dynamically adjusting the animated fixation target within the fixation zone comprises progressively shrinking the fixation zone until the fixation zone becomes a fixation point, and wherein progressively shrinking the fixation zone comprises maintaining a relative position of the animated fixation target within the fixation zone.

4. The method of claim 1, wherein multiple images are captured during one flash.

5. The method of claim 1, wherein each of the one or more images captured correspond to one of the one or more flashes.

6. The method of claim 1, further comprising:
monitoring, with an eye tracker, the eye of the examinee while dynamically adjusting, based on an output of the eye tracker, the animated fixation target within the fixation zone.

7. The method of claim 6, wherein the eye tracker tracks a location or size of the examinee's pupil, and wherein dynamically adjusting the animated fixation target is based on the location or size of the examinee's pupil.

8. The method of claim 6, further comprising:
determining that the fixation alignment is achieved based on the output of the eye tracker; and
triggering, responsive to the determination that the fixation alignment is achieved, an illumination source to emit the one or more flashes and the fundus camera to capture the one or more images of the examinee's fundus.

9. The method of claim 6, wherein the output of the eye tracker comprises a real-time video feed, the method further comprising:
projecting the real-time video feed onto the eye of the examinee.

10. The method of claim 1, further comprising:
monitoring a time of adaptation of the eye of the examinee; and
increasing an illumination of the fixation target if the time of adaptation is above a threshold.

11. The method of claim 1, further comprising:
monitoring a size of a pupil of the eye of the examinee; and
in response to determining that the pupil has stopped growing and before dark adaptation commences, triggering an illumination source to emit the one or more flashes and the fundus camera to capture the one or more images of the examinee's fundus.

12. The method of claim 1, further comprising:
monitoring a size of a pupil of the eye of the examinee; and
in response to determining that the size of the pupil exceeds a threshold value, triggering an illumination source to emit the one or more flashes and the fundus camera to capture the one or more images of the examinee's fundus.

13. A fundus camera comprising:
a display adapted to project an animated fixation target onto an eye of an examinee via an optical assembly, wherein the animated fixation target comprises a continuously moving animation;
a camera adapted to capture one or more images of the examinee's fundus; and
a control system operably coupled with the display and the camera and configured to direct the display to dynamically adjust the animated fixation target within a fixation zone for facilitating dilation of a pupil of the eye while guiding the examinee's line of sight toward fixation alignment.

14. The fundus camera of claim 13, wherein to dynamically adjust the animated fixation target within the fixation zone, the control system is configured to direct the display to progressively shrink the animated fixation target until the animated fixation target becomes a fixation point.

15. The fundus camera of claim 13, wherein the control system is further configured to monitor a time of adaptation of the eye of the examinee and increase an illumination of the fixation target if the time of adaptation is above a threshold.

16. The fundus camera of claim 13, further comprising:
an eye tracker, operably coupled with the control system and adapted to track a size of a pupil of the eye of the examinee, and wherein the control system is further configured to trigger, responsive to a determination that the size of the pupil has stopped growing and before dark adaptation commences, the camera to capture the one or more images of the examinee's fundus.

17. The fundus camera of claim 13, further comprising:
an eye tracker, operably coupled with the control system and adapted to track a size of a pupil of the eye of the examinee, and wherein the control system is further configured to trigger, responsive to a determination that the size of the pupil exceeds a threshold value, the camera to capture the one or more images of the examinee's fundus.

18. The fundus camera of claim 13, wherein multiple images are captured during one flash.

19. The fundus camera of claim 13, further comprising:
an eye tracker adapted to monitor the eye of the examinee, the eye tracker comprising an iris camera and an infrared illumination source positioned to illuminate the eye of the examinee wherein the control system directs the display to dynamically adjust, based on an output of the eye tracker, the animated fixation target within the fixation zone.

20. The fundus camera of claim 13, wherein each of the one or more images captured correspond to one of the one or more flashes.

* * * * *